Figure 1A:
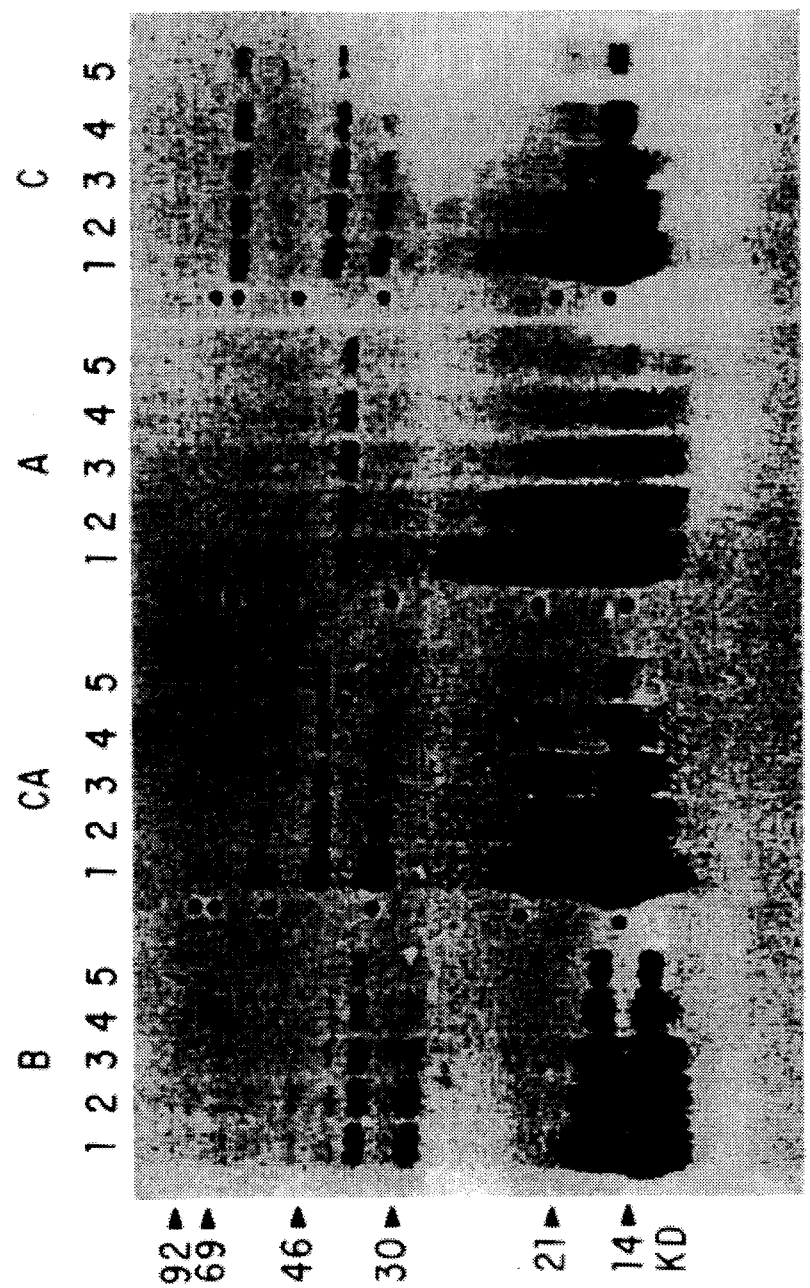

US005583046A

United States Patent [19]
Valenta et al.

[11] Patent Number: 5,583,046
[45] Date of Patent: Dec. 10, 1996

[54] BIRCH POLLEN ALLERGEN P14 FOR DIAGNOSIS AND THERAPY OF ALLERGIC DISEASES

[75] Inventors: Rudolf Valenta, Theresienfeld; Michael Duchene, Vienna; Karin Pettenburger, Vienna; Michael Breitenbach, Vienna; Dietrich Kraft, Vienna; Helmut Rumpold, Vienna; Otto Scheiner, Mariaenzersdorf, all of Austria

[73] Assignee: Biomay Biotechnik Produktions Und Handelsgesellschaft m.b.H., Linz, Austria

[21] Appl. No.: 846,992

[22] PCT Filed: Aug. 9, 1991

[86] PCT No.: PCT/EP91/01513

§ 371 Date: Jun. 6, 1992

§ 102(e) Date: Jun. 6, 1992

[87] PCT Pub. No.: WO92/03551

PCT Pub. Date: Mar. 5, 1992

[30] Foreign Application Priority Data

Aug. 13, 1990 [AT] Austria .................... 1685/90

[51] Int. Cl.$^6$ .................... C12N 15/29
[52] U.S. Cl. .................... 435/320.1; 536/23.6; 435/172.3
[58] Field of Search .................... 424/88, 91; 435/7.1, 435/7.92, 7.93, 7.94, 7.95, 320.1, 172.3; 436/501, 503, 506, 513, 518, 528; 514/12, 2; 530/324, 370; 536/27, 28, 23.6; 935/1, 4, 9, 11, 12, 22, 73, 80, 81

[56] References Cited

U.S. PATENT DOCUMENTS 4,629,706  12/1986  Hammond .................... 436/513
4,721,668  1/1988   Jones, III et al. .................... 435/6
5,116,731  5/1992   Wilhelms .................... 435/18

OTHER PUBLICATIONS

Florvaag et al. (1988), Abstract Only, "Comparative Studies on tree pollen allergens XIV" Ann. Allergy 61:392–400.
Marc-Series (1990), Abstract Only, "Mapping of Bet VI epitopes" Int. Arch. Allergy Appl. Immunol. 92:226–32.
Berger et al. (eds) (1987) "Molecular Cloning Manual" Methods in Enzymology 152:316–337, 343–349, 359–371, 451–469.
Itemmens et al. (1988) "A Comparison of the Antigenic and Allergenic Components of Birch & Alder Pollens in Scandinavia and Australia," Int. Arch. Allergy Appl. Immun. 85:27–37.
Lundberg et al (1988) "the use of poly (L–proline Sephrase in the Isolation of Profilin and Profilactin Complexes." Biochem et Biophys Acata 967:391–400.
Oreste et al., 1991, Purification and characterization of Par o 1, major antigen of *Parietaria officinalis* pollen. Int Arch Appl Immunol 96:19–27.
Geraci et al., 1994, EMBL/Gen Bank/DDBJ data bases *Parietaria Judaica* cDNA of Par 1.

Halpern, GM, "In vitro diagnosis in asthma: the state–of–the–art", Allerg. Immunool. (Paris) 1991, 23(6):255–262.
Harris Hosen, M.D., *Clinical Allergy Based on Provocative Testing*, Exposition Press, Hicksville, New York, e.g., pp. 11–29, (1978).
Clinical Experimental Allergy, vol. 20, 1990, Suppl. 1, Meeting 8–11 Jul. 1990, S. d'Abusco et al.: "Characterization of cDNA for Parietaria pollen allergens", pp. 48, see abstract OP52.
Biochimica et Biophysics Acta, vol. 967, 1988, Elsevier, U. Lindberg et al.: "The use of poly(L–proline)–sepharose in the isolation of profilin and profilactin complexes", pp. 391–400.
Int. Arch. Appl. Immunol., vol. 98, 1988, H. Breiteneder et al.: "Isolation and characterization of messenger RNA from male inflorescences and pollen of the white birch (Betula verrucosa")", pp. 19–24, see p. 21, left–hand column, Immunoblotting of aqueous BV pollen extracts.
The EMBO Journal, vol. 8, No. 7, Jul. 1989, (Eynsham, Oxford, GB) H. Breiteneder et al.: "The gene coding for the major birch pollen allergen Betvl, is highly homologous to a pea disease resistance response gene", pp. 1935–1938.
Science, vol. 253, 2 Aug. 1991, R. Valenta et al.: "Identification of profilin as a novel pollen allergen; IgE autoreactivity in sensitized individuals", pp. 557–560.
Allergy, vol. 44, No. 6, Aug. 1989, E. Jarolim et al.; "IgE and igG antibodies of patients with allergy to birch pollen as tools to define the allergen profile of Betula verrucosa", pp. 385–395.
Allergy, vol. 45, No. 6, Aug. 1990, T. Birner et al.: "Evaluation of immunotherapy–induced changes in specific IgE, IgG and IgG subclasses in birch pollen allergic patients by means of immunoblotting", pp. 418–426.
Chemical Abstracts, vol. 97:53816e "Comparative studies on tree pollen allergens, IV, Evaluation of two commercially available allergen extracts of alder (Alnus incana) and birch (Betula verrucosa) pollen", 1982, p. 480.
Chemical Abstracts, vol. 104:184481c "Comparative studies on tree pollen allergens. XII. Partial characterization of the alder (Alnus incana) pollen extract by two–dimensional IEF/SDS–PAG electrophoresis combined with electrophoretic transfer and immunoautoradiography", 1986.

(List continued on next page.)

Primary Examiner—Toni R. Scheiner
Assistant Examiner—Lora M. Green
Attorney, Agent, or Firm—Pennie & Edmonds

[57] ABSTRACT

The invention provides recombinant DNA molecules which code for proteins or polypeptides that exhibit the antigenicity of a P14 allergen of birch *Betula verrucosa* and other plants of the order Fagales, and for polypeptides comprising at least one epitope thereof, as well as nucleic acids which under stringent conditions hybridize with such DNA sequences or are derivable from such sequences by degeneracy of the genetic code. A method is provided that permits purification of P14 allergens or cross-reactive allergens by means of binding to poly(L-proline). In addition, methods are described for making the proteins and polypeptides coded by these DNA molecules and their use in the diagnosis or therapy of allergic diseases.

15 Claims, 18 Drawing Sheets

OTHER PUBLICATIONS

Chemical Abstracts, vol. 104:18392e "Immunochemical characterization of reference alder (Alnus glutinosa) and hazel (Corylus avellana) pollen extracts and the partial immunochemical identity between the major allergens of alder, birch and hazel pollens", 1986, p. 380.

Chemical Abstracts, vol. 107:2344124t "Allergologic–immunochemical investigation of various tree pollens. Part I—Characterization of antigen and allergen components in birch, beech, alder, hazel and oak pollens", 1987.

Ipsen, H. and Hansen, O. C. In: *Epitopes of Atopic Allergens*. Sehon, A. H., Kraft, D., Kunke, G. (eds) (1990) UCB, Brussels, Belgium, pp. 3–8.

Rumpold, et al. In: *Epitopes of Atopic Allergens*. Sehon, A. H., Kraft, D., Kunkel, G. (eds) (1990) UCB, Brussels, Belgium, pp. 26–28.

Valenta, et al. In: *Epitopes of Atopic Allergens*. Sehon, A. H., Kraft, D. Kunkel, G. (eds) (1990) UCB Brussels, Belgium, pp. 73–76.

Florvaag, E. et al. Int. Arch. Allergy Appl. Immunol. 75:300–308 (1984).

Florvaag, E. et al. Int. Arch. Allergy Appl. Immunol. 67:49–56 (1982).

Jarolim, et al. Int. Arch. Allergy Appl. Immunol. 90:54–60 (1989).

Hatton, T. W., Hill, R. D., Ekramoddoullah, A. K. M., Kisil, F. T. and Sehon, A. H., "Molecular Cloning of Kentucky Bluegrass (KBF) Pollen Allergens," J. Allergy Clin. Immunol., Jan. 1988) 81(1), Zusammenfassung [Abstract] Nr. 58, siehe den ganzen Artikel, Seite [p.] 183.

Lütck, H. A. et al. EMBO J. 6(1):43–48 (1987).

Thomas et al., In: *Epitopes of Atopic Allergens*. Sehon, A. H., Kraft, D., and Kunkel, G. (eds), 1990. UCB Institute of Allergy, Brussels.

Nagai, K. et al. Nature 309:810–812 (1987).

Stinson, J. R. et al. Plant Physiol. 83:442–447 (1987).

Walter, M. H. et al., Proc. Natl. Acad. Sci. USA 85:5546–5550 (Aug. 1988).

Valenta, R. et al. J. Allergy Clin. Immunol 88(6):889–894 (1991).

Tchang et al. J. Biol. Chem. 263(32):16849–16855 (1988).

Crawford et al. Proc. Natl. Acad. Sci. USA 83:8073–8076 (1986).

Scioli et al. Proc. Natl. Acad. Sci. USA 85:7661–7665 (1988).

Hemmens et al., "A Comparison of the Antigenic and Allergenic Components of Birch and Alder Pollens in Scandinavia and Australia", Int. Arch Allergy Appl. Immun. 85:27–37 (1988).

Berger et al. (eds,) "Molecular Cloning Manual" Methods in Enzymology vol. 152, pp. 316–337, 343–349, 359–371, 451–469 (1987).

Document Number 07/683,831 Name Breiteneder et al.

Document Number 07/353,844 Name Breitenbach et al.

Document Number 07,847,010 Name Breiteneder et al.

```
          10        20        30        40        50        60
CAGAGAAAGCGAAAGCTCTCCGCCACAACAAAACGAAGTAGAAGAAGAAGAGTGAGCAAG
          70        79
AGACAGAGGGAAGAGGAAA
                90        100       110       120
ATG TCG TGG CAA ACG TAC GTG GAT GAA CAT TTG ATG TGC GAT ATC
met ser trp gln thr tyr val asp glu his leu met cys asp ile
          130       140       150       160
GAC GGG CAA GCC AGC AAC TCG CTG GCA TCT GCG ATC GTC GGT CAC
asp gly gln ala ser asn ser leu ala ser ala ile val gly his
          180       190       200       210
GAT GGC TCT GTG TGG GCC CAG AGC TCT TCC TTC CCA CAG TTT AAG
asp gly ser val trp ala gln ser ser ser phe pro gln phe lys
          220       230       240       250
CCT CAG GAA ATC ACT GGT ATC ATG AAG GAC TTT GAG GAG CCG GGT
pro gln glu ile thr gly ile met lys asp phe glu glu pro gly
                270       280       290       300
CAT CTT GCT CCG ACG GGC TTA CAC CTT GGG GGC ATA AAA TAC ATG
his leu ala pro thr gly leu his leu gly gly ile lys tyr met
          310       320       330       340
GTC ATC CAG GGA GAG GCT GGT GCT GTC ATC CGT GGA AAG AAG GGA
val ile gln gly glu ala gly ala val ile arg gly lys lys gly
          360       370       380       390
TCT GGA GGT ATT ACT ATA AAG AAG ACT GGT CAA GCT CTC GTT TTT
ser gly gly ile thr ile lys lys thr gly gln ala leu val phe
          400       410       420       430
GGC ATC TAT GAA GAG CCT GTG ACA CCA GGA CAG TGC AAC ATG GTT
gly ile tyr glu glu pro val thr pro gly gln cys asn met val
          450       460       470       480
GTT GAG AGG TTG GGG GAT TAC CTT ATT GAC CAG GGC CTG TAG
val glu arg leu gly asp tyr leu ile asp gln gly leu  *
          490       500       510       520       530       540
GCAAAGGTCTATCATCATTTGGGGCTTAATTGTTTTTTTTTTTTTTTTGCTCTTATTCCC
          550       560       580       590       600       610
TTTGATTTCGGTTCCAAGTGTGCATCGATCTTCATTTGAAAGCCTTAAATTGGCAGTGAA
          620       630       640       650       660       670
GTTGTTGCAGACAATAACCATGTGAGAACTAAAACATTTGTCTTGTGTTTGGTTGTTTGA
          680       690       700       710
AAAAAAAAAAAAAAAAAAAAAAAAAAAAAAAAAAAAAAAAA
```

FIG.4

FIG.5

```
              10                  20
GAAAGCAAACTTGCAGGACCGAAG 30              40             50             60
ATG TCG TGG CAG ACG TAC GTG GAC GAG CAC CTG ATG TGC GAG ATC
met ser trp gln thr tyr val asp glu his leu met cys glu ile
                   80              90            100           110
GAG GGC CAC CAC CTC GCC TCG GCG GCC ATC CTC GGC CAC GAC GGC
glu gly his his leu ala ser ala ala ile leu gly his asp gly
         120             130            140            150
ACC GTC TGG GCC CAG AGC GCC GAC TTC CCC CAG TTC AAG CCT GAG
thr vla trp ala gln ser ala asp phe pro gln phe lys pro glu
                  170            180            190            200
GAG ATC ACC GGC ATC ATG AAG GAT TTC GAC GAG CCG GGG CAC CTC
glu ile thr gly ile met lys asp phe asp glu pro gly his leu
         210             220            230            240
GCC CCC ACC GGC ATG TTC GTC GCA GGT GCC AAG TAC ATG GTC ATC
ala pro thr gly met phe val ala gly ala lys tyr met val ile
                  260            270            280            290
CAG GGT GAA CCC GGT CGC GTC ATC CGT GGC AAG AAG GGA GCA GGA
gln gly glu pro gly arg val ile arg gly lys lys gly ala gly
         300             310            320            330
GGC ATC ACC ATA AAG AAG ACC GGG CAG GCG CTG GTC GTC GGC ATC
gly ile thr ile lys lys thr gly gln ala leu val val gly ile
                  350            360            370            380
TAT GAC GAG CCC ATG ACC CCT GGG CAG TGC AAC ATG GTG GTG GAG
tyr asp glu pro met thr pro gly gln cys asn met val val glu
         390             400            410            420
AGG CTT GGC GAC TAC CTC GTT GAA CAA GGC ATG TAG
arg leu gly asp tyr leu val glu gln gly met  *

430       440       450       460       470       480
ACTGGCTGATCCATGGCTTCCACGTCTCCACGATCGATGATGATCATACAGTTTTTCACG
           490       500       510       520       530       540
TTCTTTTAAACATCTATTGGAATATATATGGGGCTTCTCCTCTTTTACCGGCTCTGGTCA
           550       560       570       580       590       600
TGGATCACTGATGACCAGTTGCTCTGGAAGTTTCATTTGTAATGCCATCTTGGCTTTCTA
           610       620       630       640
TCTTCTTCAATGTTTTTTTTTTCTTTTCGGTTAAAAAAAAA
```

FIG.16

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 700 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Betula verrucosa ( v i i ) IMMEDIATE SOURCE:
        ( A ) POLLEN FROM ALLERGON AB, ENGELHOLM, SWEDEN ( x i ) SEQUENCE DESCRIPTION: SEQ ID NO:1:

```
CAGAGAAAGC  GAAAGCTCTC  CGCCACAACA  AAACGAAGTA  GAAGAAGAAG  AGTGAGCAAG      60

AGACAGAGGG  AAGAGGAAAA  TGTCGTGGCA  AACGTACGTG  GATGAACATT  TGATGTGCGA     120

TATCGACGGG  CAAGCCAGCA  ACTCGCTGGC  ATCTGCGATC  GTCGGTCACG  ATGGCTCTGT     180

GTGGGCCCAG  AGCTCTTCCT  TCCCACAGTT  TAAGCCTCAG  GAAATCACTG  GTATCATGAA     240

GGACTTTGAG  GAGCCGGGTC  ATCTTGCTCC  GACGGGCTTA  CACCTTGGGG  GCATAAAATA     300

CATGGTCATC  CAGGGAGAGG  CTGGTGCTGT  CATCCGTGGA  AAGAAGGGAT  CTGGAGGTAT     360

TACTATAAAG  AAGACTGGTC  AAGCTCTCGT  TTTTGGCATC  TATGAAGAGC  CTGTGACACC     420

AGGACAGTGC  AACATGGTTG  TTGAGAGGTT  GGGGGATTAC  CTTATTGACC  AGGGCCTGTA     480

GGCAAAGGTC  TATCATCATT  TGGGGCTTAA  TTGTTTTTTT  TTTTTTTTTG  CTCTTATTCC     540
```

| | | | | | | | |
|---|---|---|---|---|---|---|---|
| CTTTGATTTC | GGTTCCAAGT | GTGCATCGAT | CTTCATTTGA | AAGCCTTAAA | TTGGCAGTGA | | 600 |
| AGTTGTTGCA | GACAATAACC | ATGTGAGAAC | TAAAACATTT | GTCTTGTGTT | TGGTTGTTTG | | 660 |
| AAAAAAAAAA | AAAAAAAAAA | AAAAAAAAAA | AAAAAAAAA | | | | 700 |

( 2 ) INFORMATION FOR SEQ ID NO:2:

( i ) SEQUENCE CHARACTERISTICS:
        ( A ) LENGTH: 398 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Betula verrucosa ( v i i ) IMMEDIATE SOURCE:
        ( A ) POLLEN FROM ALLERGON AB, ENGELHOLM, SWEDEN ( x i ) SEQUENCE DESCRIPTION: SEQ ID NO:2:

| | | | | | | | |
|---|---|---|---|---|---|---|---|
| ATGTCGTGGC | AAACGTACGT | GGATGAACAT | TTGATGTGCG | ATATCGACGG | GCAAGCCAGC | | 60 |
| AACTCGCTGG | CATCTGCGAT | CGTCGGTCAC | GATGGCTCTG | TGTGGGCCCA | GAGCTCTTCC | | 120 |
| TTCCCACAGT | TTAAGCCTCA | GGAAATCACT | GGTATCATGA | AGGACTTTGA | GGAGCCGGGT | | 180 |
| CATCTTGCTC | CGACGGGCTT | ACACCTTGGG | GGCATAAAAT | ACATGGTCAT | CCAGGGAGAG | | 240 |
| GCTGGTGCTG | TCATCCGTGG | AAAGAAGGGA | TCTGGAGGTA | TTACTATAAA | GAAGACTGGT | | 300 |
| CAAGCTCTCG | TTTTTGGCAT | CTATGAAGAG | CCTGTGACAC | CAGGACAGTG | CAACATGGTT | | 360 |
| GTTGAGAGGT | TGGGGGATTA | CCTTATTGAC | CAGGGCTG | | | | 398 |

( 2 ) INFORMATION FOR SEQ ID NO:3:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Betula verrucosa ( i x ) FEATURE:
        ( D ) OTHER INFORMATION: Amino acid sequence identity
            with profilin of other organisms is as follows:
            30% with human profilin, 28% with calf and mouse,
            26% with yeast and 25% with Acanthamoeba ( x i ) SEQUENCE DESCRIPTION: SEQ ID NO:3:

| Met | Ser | Trp | Gln | Thr | Tyr | Val | Asp | Glu | His | Leu | Met | Cys | Asp | Ile | Asp |
|---|---|---|---|---|---|---|---|---|---|---|---|---|---|---|---|
| 1 | | | | 5 | | | | | 10 | | | | | 15 | |
| Gly | Gln | Ala | Ser | Asn | Ser | Leu | Ala | Ser | Ala | Ile | Val | Gly | His | Asp | Gly |
| | | | 20 | | | | | 25 | | | | | 30 | | |
| Ser | Val | Trp | Ala | Gln | Ser | Ser | Ser | Phe | Pro | Gln | Phe | Lys | Pro | Gln | Glu |
| | | | 35 | | | | | 40 | | | | 45 | | | |
| Ile | Thr | Gly | Ile | Met | Lys | Asp | Phe | Glu | Glu | Pro | Gly | His | Leu | Ala | Pro |
| | | 50 | | | | 55 | | | | | 60 | | | | |
| Thr | Gly | Leu | His | Leu | Gly | Gly | Ile | Lys | Tyr | Met | Val | Ile | Gln | Gly | Glu |

```
                 65                            70                            75                            80
         Ala  Gly  Ala  Val  Ile  Arg  Gly  Lys  Lys  Gly  Ser  Gly  Gly  Ile  Thr  Ile
                        85                           90                      95

Lys  Lys  Thr  Gly  Gln  Ala  Leu  Val  Phe  Gly  Ile  Tyr  Glu  Glu  Pro  Val
                        100                          105                     110

Thr  Pro  Gly  Gln  Cys  Asn  Met  Val  Val  Glu  Arg  Leu  Gly  Asp  Tyr  Leu
                        115                          120                     125

Ile  Asp  Gln  Gly  Leu
                        130
```

( 2 ) INFORMATION FOR SEQ ID NO:4:

( i ) SEQUENCE CHARACTERISTICS:
        ( A ) LENGTH: 140 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Mouse (murine)

( i x ) FEATURE:
        ( D ) OTHER INFORMATION: 28% identical with the P14
            allergen of birch (Betula verrucosa)

( x ) PUBLICATION INFORMATION: Reference 12

( x i ) SEQUENCE DESCRIPTION: SEQ ID NO:4:

```
         Met  Ala  Gly  Trp  Asn  Ala  Tyr  Ile  Asp  Ser  Leu  Met  Ala  Asp  Gly  Thr
         1                   5                        10                      15

Cys  Gln  Asp  Ala  Ala  Ile  Val  Gly  Tyr  Lys  Asp  Ser  Pro  Ser  Val  Trp
                        20                           25                      30

Ala  Ala  Val  Pro  Gly  Lys  Thr  Phe  Val  Ser  Ile  Thr  Pro  Ala  Glu  Val
                        35                           40                      45

Gly  Val  Leu  Val  Gly  Lys  Asp  Arg  Ser  Ser  Phe  Phe  Val  Asn  Gly  Leu
                   50                      55                      60

Thr  Leu  Gly  Gly  Gln  Lys  Cys  Ser  Val  Ile  Arg  Asp  Ser  Leu  Leu  Gln
         65                       70                      75                      80

Asp  Gly  Glu  Phe  Thr  Met  Asp  Leu  Arg  Thr  Lys  Ser  Thr  Gly  Gly  Ala
                             85                      90                      95

Pro  Thr  Phe  Asn  Val  Thr  Val  Thr  Met  Thr  Ala  Lys  Thr  Leu  Val  Leu
                        100                          105                     110

Leu  Met  Gly  Lys  Glu  Gly  Val  His  Gly  Gly  Leu  Ile  Asn  Lys  Lys  Cys
                        115                          120                     125

Tyr  Glu  Met  Ala  Ser  His  Leu  Arg  Arg  Ser  Gln  Tyr
                   130                     135                     140
```

( 2 ) INFORMATION FOR SEQ ID NO:5:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Calf (bovine)

( i x ) FEATURE:

(D) OTHER INFORMATION: 28% identical with the P14
     allergen of birch (Betula verrucosa)

(x) PUBLICATION INFORMATION: Reference 14

(xi) SEQUENCE DESCRIPTION: SEQ ID NO:5:

| Ala | Gly | Trp | Asn | Ala | Tyr | Ile | Asp | Asn | Leu | Met | Ala | Asp | Gly | Thr | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Asp | Ala | Ala | Ile | Val | Gly | Tyr | Lys | Asp | Ser | Pro | Ser | Val | Trp | Ala |
|     |     |     | 20  |     |     |     |     | 25  |     |     |     |     | 30  |     |     |

| Ala | Val | Pro | Gly | Lys | Thr | Phe | Val | Asn | Ile | Thr | Pro | Ala | Glu | Val | Gly |
|     |     | 35  |     |     |     |     | 40  |     |     |     |     | 45  |     |     |     |

| Ile | Leu | Val | Gly | Lys | Asp | Arg | Ser | Ser | Phe | Phe | Val | Asn | Gly | Leu | Thr |
|     | 50  |     |     |     |     | 55  |     |     |     |     | 60  |     |     |     |     |

| Leu | Gly | Gly | Gln | Lys | Cys | Ser | Val | Ile | Arg | Asp | Ser | Leu | Leu | Gln | Asp |
| 65  |     |     |     |     | 70  |     |     |     |     | 75  |     |     |     |     | 80  |

| Gly | Glu | Phe | Thr | Met | Asp | Leu | Arg | Thr | Lys | Ser | Thr | Gly | Gly | Ala | Pro |
|     |     |     |     | 85  |     |     |     |     | 90  |     |     |     |     | 95  |     |

| Thr | Phe | Asn | Ile | Thr | Val | Thr | Met | Thr | Ala | Lys | Thr | Leu | Val | Leu | Leu |
|     |     |     | 100 |     |     |     |     | 105 |     |     |     |     | 110 |     |     |

| Met | Gly | Lys | Gln | Gly | Val | His | Gly | Gly | Met | Ile | Asn | Lys | Lys | Cys | Tyr |
|     |     |     | 115 |     |     |     |     | 120 |     |     |     |     | 125 |     |     |

| Glu | Met | Ala | Ser | His | Leu | Arg | Arg | Ser | Gln | Tyr |
|     |     |     | 130 |     |     |     | 135 |     |     |     |

(2) INFORMATION FOR SEQ ID NO:6:

(i) SEQUENCE CHARACTERISTICS:
      (A) LENGTH: 140 amino acids
      (B) TYPE: amino acid
      (D) TOPOLOGY: linear (ii) MOLECULE TYPE: peptide (iii) HYPOTHETICAL: NO (vi) ORIGINAL SOURCE:
      (A) ORGANISM: Human (Homo sapiens)

(ix) FEATURE:
      (D) OTHER INFORMATION: 30% identical with the P14
         allergen of birch (Betula verrucosa)

(x) PUBLICATION INFORMATION: Reference 13

(xi) SEQUENCE DESCRIPTION: SEQ ID NO:6:

| Met | Ala | Gly | Trp | Asn | Ala | Tyr | Ile | Asp | Asn | Leu | Met | Ala | Asp | Gly | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Cys | Gln | Asp | Ala | Ala | Ile | Val | Gly | Tyr | Lys | Asp | Ser | Pro | Ser | Val | Trp |
|     |     |     | 20  |     |     |     |     | 25  |     |     |     |     | 30  |     |     |

| Ala | Ala | Val | Pro | Gly | Lys | Thr | Phe | Val | Asn | Ile | Thr | Pro | Ala | Glu | Val |
|     |     | 35  |     |     |     |     | 40  |     |     |     |     | 45  |     |     |     |

| Gly | Val | Leu | Val | Gly | Lys | Asp | Arg | Ser | Ser | Phe | Tyr | Val | Asn | Gly | Leu |
|     | 50  |     |     |     |     | 55  |     |     |     |     | 60  |     |     |     |     |

| Thr | Leu | Gly | Gly | Gln | Lys | Cys | Ser | Val | Ile | Arg | Asp | Ser | Leu | Leu | Gln |
| 65  |     |     |     |     | 70  |     |     |     |     | 75  |     |     |     |     | 80  |

| Asp | Gly | Glu | Phe | Ser | Met | Asp | Leu | Arg | Thr | Lys | Ser | Thr | Gly | Gly | Ala |
|     |     |     |     | 85  |     |     |     |     | 90  |     |     |     |     | 95  |     |

| Pro | Thr | Phe | Asn | Val | Thr | Val | Thr | Lys | Thr | Asp | Lys | Thr | Leu | Val | Leu |
|     |     |     | 100 |     |     |     |     | 105 |     |     |     |     | 110 |     |     |

| Leu | Met | Gly | Lys | Glu | Gly | Val | His | Gly | Gly | Leu | Ile | Asn | Lys | Lys | Cys |
|     |     |     | 115 |     |     |     |     | 120 |     |     |     |     | 125 |     |     |

```
      Tyr  Glu  Met  Ala  Ser  His  Leu  Arg  Arg  Ser  Gln  Tyr
           130                 135                     140
```

(2) INFORMATION FOR SEQ ID NO:7:

(i) SEQUENCE CHARACTERISTICS:
        (A) LENGTH: 126 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (A) ORGANISM: Yeast (ix) FEATURE:
        (D) OTHER INFORMATION: 26% identical with the P14
            allergen of birch (Betula verrucosa)

(x) PUBLICATION INFORMATION: Reference 11

(xi) SEQUENCE DESCRIPTION: SEQ ID NO:7:

```
Met  Ser  Trp  Gln  Ala  Tyr  Thr  Asp  Asn  Leu  Ile  Gly  Thr  Gly  Lys  Val
1                    5                        10                       15

Asp  Lys  Ala  Val  Ile  Tyr  Ser  Arg  Ala  Gly  Asp  Ala  Val  Trp  Ala  Thr
               20                        25                      30

Ser  Gly  Gly  Leu  Ser  Leu  Gln  Pro  Asn  Glu  Ile  Gly  Glu  Ile  Val  Gln
          35                        40                       45

Gly  Phe  Asp  Asn  Pro  Ala  Gly  Leu  Gln  Ser  Asn  Gly  Leu  His  Ile  Gln
          50                        55                       60

Gly  Gln  Lys  Phe  Met  Leu  Leu  Arg  Ala  Asp  Arg  Ser  Ile  Tyr  Gly
65                       70                        75                       80

Arg  His  Asp  Ala  Glu  Gly  Val  Val  Cys  Val  Arg  Thr  Lys  Gln  Thr  Val
               85                        90                       95

Ile  Ile  Ala  His  Tyr  Pro  Pro  Thr  Val  Gln  Ala  Gly  Glu  Ala  Thr  Lys
               100                       105                      110

Ile  Val  Glu  Gln  Leu  Ala  Asp  Tyr  Leu  Ile  Gly  Val  Gln  Tyr
          115                       120                      125
```

(2) INFORMATION FOR SEQ ID NO:8:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (A) ORGANISM: Acanthamoeba (ix) FEATURE:
        (D) OTHER INFORMATION: 25% identical with the P14
            allergen of birch (Betula verrucosa)

(x) PUBLICATION INFORMATION: Reference 10

(xi) SEQUENCE DESCRIPTION: SEQ ID NO:8:

```
Thr  Trp  Gln  Ser  Tyr  Val  Asp  Thr  Asn  Leu  Val  Gly  Thr  Gly  Ala  Val
1                    5                        10                       15

Thr  Gln  Ala  Ala  Ile  Leu  Gly  Leu  Asp  Gly  Asn  Thr  Trp  Ala  Ser  Phe
               20                        25                      30
```

|       |     |     |     |     |     |     |     |     |     |     |     |     |     |
|-------|-----|-----|-----|-----|-----|-----|-----|-----|-----|-----|-----|-----|-----|
| Ala | Gly | Phe | Ala | Val | Thr | Pro | Ala | Gln | Gly | Thr | Thr | Leu | Ala | Gly | Ala |
|     |     | 35  |     |     |     |     | 40  |     |     |     |     | 45  |     |     |     |
| Phe | Asn | Asn | Ala | Asp | Ala | Ile | Arg | Ala | Gly | Gly | Phe | Asp | Leu | Ala | Gly |
|     | 50  |     |     |     |     | 55  |     |     |     |     | 60  |     |     |     |     |
| Val | His | Tyr | Val | Thr | Leu | Arg | Ala | Asp | Asp | Arg | Ser | Ile | Tyr | Gly | Lys |
| 65  |     |     |     |     | 70  |     |     |     |     | 75  |     |     |     |     | 80  |
| Lys | Gly | Ala | Ser | Gly | Val | Ile | Thr | Val | Lys | Thr | Ser | Lys | Ser | Ile | Leu |
|     |     |     |     | 85  |     |     |     |     | 90  |     |     |     |     | 95  |     |
| Val | Gly | Val | Tyr | Asn | Glu | Lys | Ile | Gln | Pro | Gly | Thr | Ala | Ala | Asn | Val |
|     |     |     | 100 |     |     |     |     | 105 |     |     |     |     | 110 |     |     |
| Val | Glu | Lys | Leu | Ala | Asp | Tyr | Leu | Ile | Gly | Gln | Gly | Phe |     |     |     |
|     |     | 115 |     |     |     |     | 120 |     |     |     |     | 125 |     |     |     |

( 2 ) INFORMATION FOR SEQ ID NO:9:

( i ) SEQUENCE CHARACTERISTICS:
        ( A ) LENGTH: 641 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Phleum pratense ( v i i ) IMMEDIATE SOURCE:
        ( A ) POLLEN FROM ALLERGON AB, ENGELHOLM, SWEDEN ( x i ) SEQUENCE DESCRIPTION: SEQ ID NO:9:

| | | | | | |
|---|---|---|---|---|---|
| GAAAGCAAAC | TTGCAGGACC | GAAGATGTCG | TGGCAGACGT | ACGTGGACGA | GCACCTGATG | 60 |
| TGCGAGATCG | AGGGCCACCA | CCTCGCCTCG | GCGGCCATCC | TCGGCCACGA | CGGCACCGTC | 120 |
| TGGGCCCAGA | GCGCCGACTT | CCCCCAGTTC | AAGCCTGAGG | AGATCACCGG | CATCATGAAG | 180 |
| GATTTCGACG | AGCCGGGGCA | CCTCGCCCCC | ACCGGCATGT | TCGTCGCAGG | TGCCAAGTAC | 240 |
| ATGGTCATCC | AGGGTGAACC | CGGTCGCGTC | ATCCGTGGCA | AGAAGGGAGC | AGGAGGCATC | 300 |
| ACCATAAAGA | AGACCGGGCA | GGCGCTGGTC | GTCGGCATCT | ATGACGAGCC | CATGACCCCT | 360 |
| GGGCAGTGCA | ACATGGTGGT | GGAGAGGCTT | GGCGACTACC | TCGTTGAACA | AGGCATGTAG | 420 |
| ACTGGCTGAT | CCATGGCTTC | CACGTCTCCA | CGATCGATGA | TGATCATACA | GTTTTTCACG | 480 |
| TTCTTTTAAA | CATCTATTGG | AATATATATG | GGGCTTCTCC | TCTTTTACCG | GCTCTGGTCA | 540 |
| TGGATCACTG | ATGACCAGTT | GCTCTGGAAG | TTTCATTTGT | AATGCCATCT | TGGCTTTCTA | 600 |
| TCTTCTTCAA | TGTTTTTTTT | TTCTTTTCGG | TTAAAAAAAA | A | | 641 |

( 2 ) INFORMATION FOR SEQ ID NO:10:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Phleum pratense (vii) IMMEDIATE SOURCE:
  (A) POLLEN FROM ALLERGON AB, ENGELHOLM, SWEDEN (xi) SEQUENCE DESCRIPTION: SEQ ID NO:10:

| | | | | | |
|---|---|---|---|---|---|
| ATGTCGTGGC | AGACGTACGT | GGACGAGCAC | CTGATGTGCG | AGATCGAGGG | CCACCACCTC | 60 |
| GCCTCGGCGG | CCATCCTCGG | CCACGACGGC | ACCGTCTGGG | CCCAGAGCGC | CGACTTCCCC | 120 |
| CAGTTCAAGC | CTGAGGAGAT | CACCGGCATC | ATGAAGGATT | TCGACGAGCC | GGGGCACCTC | 180 |
| GCCCCCACCG | GCATGTTCGT | CGCAGGTGCC | AAGTACATGG | TCATCCAGGG | TGAACCCGGT | 240 |
| CGCGTCATCC | GTGGCAAGAA | GGGAGCAGGA | GGCATCACCA | TAAAGAAGAC | CGGGCAGGCG | 300 |
| CTGGTCGTCG | GCATCTATGA | CGAGCCCATG | ACCCTGGGC | AGTGCAACAT | GGTGGTGGAG | 360 |
| AGGCTTGGCG | ACTACCTCGT | TGAACAAGGC | ATG | | | 393 |

(2) INFORMATION FOR SEQ ID NO:11:

(i) SEQUENCE CHARACTERISTICS:
    (A) LENGTH: 131 amino acids
    (B) TYPE: amino acid
    (D) TOPOLOGY: linear (ii) MOLECULE TYPE: peptide (iii) HYPOTHETICAL: NO (vi) ORIGINAL SOURCE:
    (A) ORGANISM: Phleum pratense (ix) FEATURE:
    (D) OTHER INFORMATION: Amino acid identity with P14
         allergen from Betula verrucosa is 77%

(xi) SEQUENCE DESCRIPTION: SEQ ID NO:11:

```
Met Ser Trp Gln Thr Tyr Val Asp Glu His Leu Met Cys Glu Ile Glu
 1               5                  10                 15

Gly His His Leu Ala Ser Ala Ala Ile Leu Gly His Asp Gly Thr Val
            20                  25                 30

Trp Ala Gln Ser Ala Asp Phe Pro Gln Ile Lys Pro Glu Glu Ile Thr
        35                  40                 45

Gly Ile Met Lys Asp Phe Asp Glu Pro Gly His Leu Ala Pro Thr Gly
    50                  55                 60

Met Phe Val Ala Gly Ala Lys Tyr Met Val Ile Gln Gly Glu Pro Gly
65                  70                 75                 80

Arg Val Ile Arg Gly Lys Lys Gly Ala Gly Gly Ile Thr Ile Lys Lys
                85                  90                 95

Thr Gly Gln Ala Leu Val Val Gly Ile Tyr Asp Glu Pro Met Thr Pro
             100                 105                110

Gly Gln Cys Asn Met Val Val Glu Arg Leu Gly Asp Tyr Leu Val Glu
         115                 120                 125

Gln Gly Met
    130
```

BIRCH POLLEN ALLERGEN P14 FOR DIAGNOSIS AND THERAPY OF ALLERGIC DISEASES

1. FIELD OF THE INVENTION

The invention provides recombinant DNA molecules which code for polypeptides, and the polypeptides per se, that have at least one epitope of a P14 pollen allergen of a tree of the order Fagales, particularly birch (*Betula verrucosa*), or the entire P14 allergen protein, and exhibit the same or similar antigenicity as a P14 allergen. The invention also provides replicable microbial expression vehicles and microorganisms for use in processes for producing such allergenic polypeptides. Methods are provided for purification of P14 allergen as well as for the diagnosis and therapy of allergic diseases using the synthetic polypeptides of the invention.

2. BACKGROUND OF THE INVENTION

In the springtime large parts of the populations of Central, Eastern and Northern Europe, America and Australia suffer from allergic symptoms (rhinitis, conjunctivitis, dermatitis and pollen asthma). Proteins which can be isolated from pollen of trees of the order Fagales, in particular from pollen of birch, alder, hazel, hornbeam and oak, are responsible for most of these allergic symptoms (1).

At least 10% of the population suffers from pollen allergies at various times and to varying extent. These allergies are mediated by IgE antibodies which react with pollen proteins. The possibility exists for a therapy for pollen allergies by hyposensitization, i.e., by the regular and slowly increasing administration of the proteins producing the allergy.

Diagnostic methods for allergic diseases, such as RIA (radioimmunoassay), IRMA (immuno-radiometric assay), RAST (radio-allergosorbent test), ELISA (enzyme-linked immunosorbent assay), magnetic allergoabsorbent test, immunoblots, LIA (luminescence immunosay), histamine release assays and others depend greatly upon the availability of pure allergens. Protein extracts from pollen isolated from natural sources are difficult to standardize because preparations vary from batch to batch. For example, they may contain unwanted constituents, and/or certain proteins may be lost in the extraction procedure and be missing from the final separation (2). Clearly, diagnostic tests which employ well defined allergens that can be reproducibly prepared would be superior to tests which employ raw pollen extracts with an insufficiently defined mixture of allergens and other components. Recombinant DNA production of allergenic polypeptides, or allergenic fragments thereof, would allow more reproducible preparations of allergens of defined content for standardized diagnostic and therapeutic methods.

Allergens may be purified to homogenity from pollen by known protein/chemical methods, for example, by means of affinity chromatography (3). These methods are relatively costly and require pollen as an ill-defined source which cannot be standardized. It would, therefore, be cheaper and more efficient to use recombinant DNA methods to produce an allergenic protein, or fragments of that protein.

Hyposensitization has proved to be an effective therapy in allergic diseases. This therapy consists of parenteral or oral administration of allergens in increasing doses over a fairly long period of time. Like diagnostic methods, it requires pure and well defined allergens. The use of purified recombinant allergens or synthetic peptides would greatly reduce the risk of sensitizing patients to unwanted components.

3. SUMMARY OF THE INVENTION

Figure 1B:
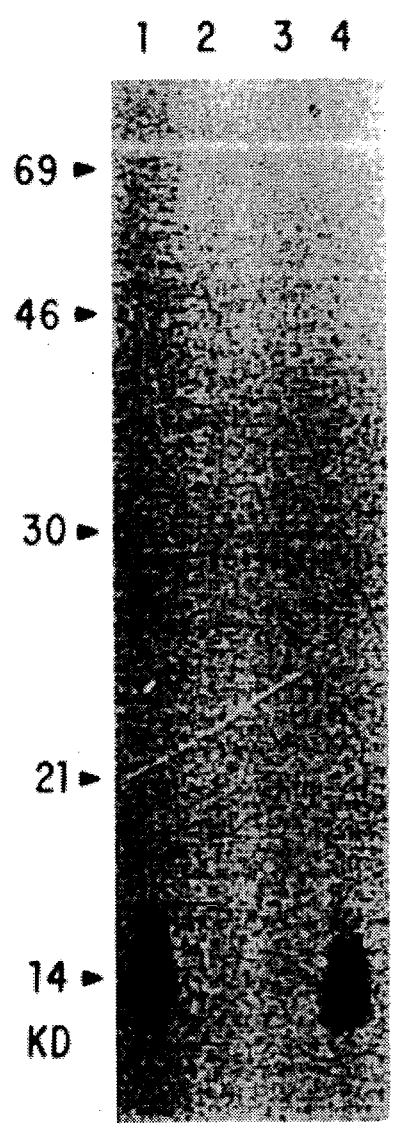

This invention concerns pollen allergens, for example, of white birch (*Betula verrucosa*), called P14. These pollen allergens are immunologically closely related to allergens which occur in pollen of far distantly related plant species, particularly in trees of the Fagales order (birch, alder, hazel, hornbeam and oak), in grasses and weeds. The cross-reactivity of IgE antibodies of patients to these pollen allergens is illustrated in FIGS. 1A and 1B.

The present invention provides recombinant DNA molecules which contain a nucleotide sequence that codes for a polypeptide which exhibits the same or similar antigenic properties as a natural allergen, P14, which occurs in trees of the order Fagales and other pollen producing plants, or a polypeptide which comprises at least one epitope of such allergens. The invention provides the complete cDNA sequence of a P14 allergen and hence the complete deduced amino acid sequence. Additionally, the invention includes (a) nucleotide sequences which hybridize with such a cDNA sequence under high stringency and encode a polypeptide having at least one epitope of a P14 allergen and (b) nucleotide sequences which can be derived from such allergenic polypeptides by degeneracy of the genetic code. This nucleotide sequence can be expressed as a P14 allergen, or as a polypeptide which comprises at least one epitope thereof. In a preferred embodiment, this cDNA sequence contains the whole sequence or parts of the sequence set forth in the Sequence Listing as SEQ ID NO:2.

As concerns their IgE binding, pollens of birch, alder, hazel, hornbeam, oak, grasses and weeds possess similar allergens as the P14 allergen. The present invention therefore relates not only to a P14 allergen of birch, but as well to P14 pollen allergens of other species which are coded by DNA sequences that are able to hybridize with the nucleotide sequence of a birch P14 allergen under stringent conditions or can be derived from such polypeptide by degeneracy of the genetic code. Hybridization of a polynucleotide with another polynucleotide under stringent conditions requires at least a 60% identity between such polynucleotides at the nucleic acid level.

Such stringent conditions entail washing of hybridized nitrocellulose filters as follows:

a) For DNA/DNA and DNA/RNA hybridizations: A temperature of 55° C., a salt concentration of 150 mM NaCl and 15 mM Na$_3$citrate×2 H$_2$O, at pH 7,0, and SDS (Sodium Dodecyl Sulfate) detergent at a concentration of 0,1% (w/v).

(b) For oligodeoxynucleotides/DNA hybridizations: A temperature of 55° C., a salt concentration of 1M NaCl and 10 mM Na$_3$citrate×2 H$_2$O, at pH 7,0, and SDS (Sodium Dodecyl Sulfate) detergent at a concentration of 0,5% (w/v). In this context "oligodeoxynucleotide" refers to an oligomer of a single stranded DNA of up to 100 nucleotides in length.

In addition, this invention provides expression plasmids that contain a nucleotide sequence as described above and those cells which harbor these expression plasmids.

This invention also provides compositions containing synthetic polypeptides which exhibit the antigenicity of parts or of the whole of a birch P14 allergen or of allergens of other plants which, because of a high degree (at least 50%) of amino acid homology, exhibit antigenic crossreactivity to parts or to all of a birch P14 allergen, i.e., antibodies or cellular antigen binding sites which are actually directed to birch P14 allergen are likewise able to bind to these molecules. These synthetic polypeptides include fusion and nonfusion polypeptides which contain a polypeptide portion that possesses the antigenicity of a part or of all of a P14 allergen. The method for preparing such synthetic polypeptides comprises the steps of culturing of prokaryotic or eukaryotic host cells which contain an expression plasmid described above and purification of the synthetic polypeptide(s) from the culture.

The term "synthetic" here alternatively includes polypeptides which are prepared by cloning and expression of the nucleotide sequences described here or by chemical synthesis of polypeptides encoded by these nucleotide sequences.

The synthetic polypeptides which are produced according to this invention exhibit antigenicity the same as or similar to the native allergen. As shown below, a cDNA clone coding for a birch P14 can be used to produce a nonfusion polypeptide which reacts with IgE in the sera of allergic persons. It is therefore possible to use this polypeptide as an antigen in diagnostic tests (such as RAST, ELISA, Immunoblots and others known in the art and referred to above) and as a component of therapeutic agents in hyposensitization therapy.

In particular, the synthetic allergens can be used as diagnostic reagents in vitro and in vivo, since their antigenicity corresponds to that of the native P14 pollen allergens and they are therefore able to bind IgE in sera of persons suffering from P14 pollen allergy.

It is therefore one of the objects of the present invention to provide a method for the preparation of pollen allergens, in particular for birch P14 allergens, so as to have this family of allergens available for diagnostic tests for detection of the corresponding allergy and, alternatively, for hyposensitization therapy.

In addition, as shown below, birch P14 cDNA was expressed in two prokaryotic expression systems in *Escherichia coli*, and the IgE-binding capacity of the expressed polypeptides, a fusion protein and a nonfusion protein, was demonstrated. This expression can also be achieved in any other microorganism (e.g., eukaryotic cells). The IgE-binding capacity was also demonstrated for a partial sequence which was expressed, using lambda gt11, as a β-galactosidase fusion protein. In this way it was demonstrated that this partial sequence represents at least one IgE-binding epitope. In addition, it may be concluded from the results of IgE immunoblots, cross-inhibition tests, clinical tests and Northern ((RNA) blots (4–9) (FIGS. 1A, 1B and 3) that homologous IgE-binding polypeptides exist in the pollen of closely related trees of the order Fagales and for distantly related pollen producing plants. For this reason this invention provides polypeptides which exhibit the same or similar antigenicity as the related P14 pollen allergens of birch, alder, hazel, hornbeam, oak, grasses and weeds.

Figure 5:
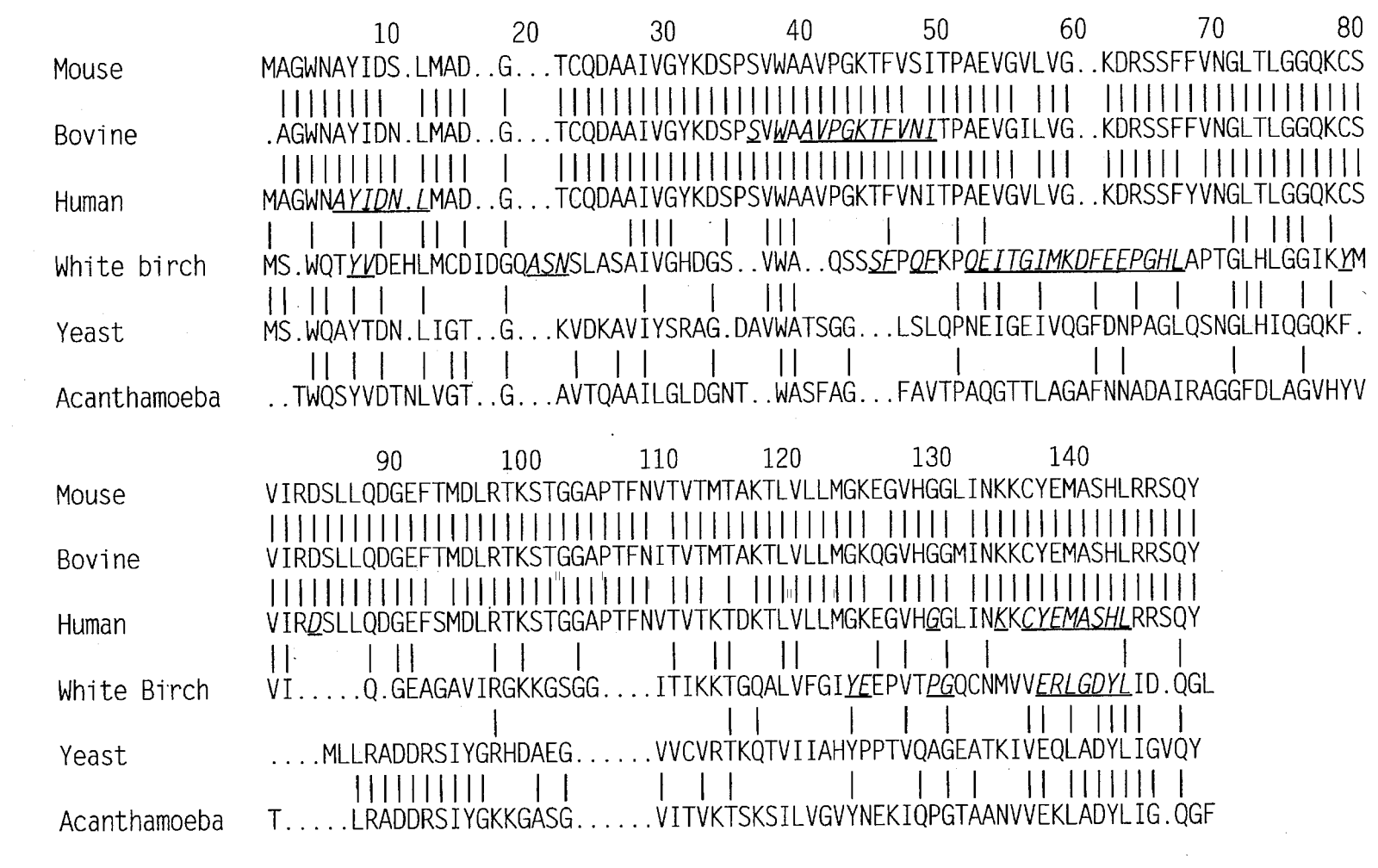
Figure 12:
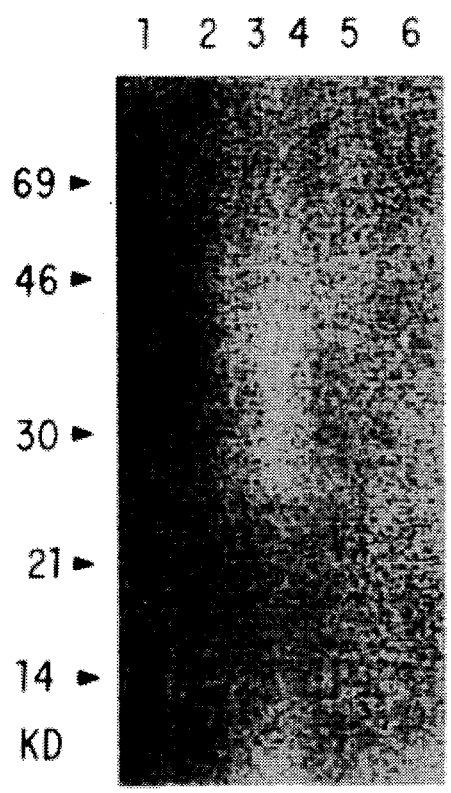

A computer search in the available sequence data banks (EMBL, MIPSX, Swissprot) for proteins whose sequences share homology with birch P14 revealed a significant homology between P14 and a cytoskeletal protein (profilin) which is present in a variety of eukaryotes (10–14) (FIG. 5). This homology raises the possibility of the cross-reactivity of IgE antibodies of patients with human profilin. This autoreactivity has been demonstrated (FIG. 12).

In this way, a molecular system is provided which permits testing the hypothesis: whether autoimmune mechanisms play a role in allergic and atopic diseases. Initial data show that patients whose IgE antibodies react with P14 represent a group that suffers from allergic symptoms during a large part of the year and who do not respond satisfactorily to immunotherapy or conventional therapy. It follows from this that P14, or recombinant or chemically synthesized IgE-binding polypeptides with sequences that match the sequence deduced from P14 cDNA, can be used to characterize a certain group of multivalent allergics as well as a prognostic markers for hyposensitization therapy.

In addition, this invention presents an efficient method for the production and purification of pollen protein as well as of recombinant or synthetic P14 polypeptide or allergenic fragments thereof. The purification method is based on the affinity of profilin polypeptides for poly(L-proline) (15, 16), and the present inventors' showing of homology between profilins and P14 allergens. Since the binding of pollen protein and of recombinant P14 to poly(L-proline) has been shown herein (FIGS. 8, 9 and 10), a method is thereby provided for immobilizing (and affinity separation of) this allergen. Thus, certain diagnostic tests can be set up (for example, poly(L-proline) may be used instead of an antibody for binding profilin in ELISAs). Likewise, forms of therapy are possible which by means of poly(L-proline) bind P14 and analogous polypeptide allergens. Since there are indications that patients who suffer from autoimmune diseases form antibodies against P14, this polypeptide or homologous polypeptides could be used for diagnosis or therapy of these diseases.

The invention further comprises a method for detecting in vitro the cellular reaction to P14 allergen by contacting mammalian cells with the recombinant P14 allergen of the invention and detecting the reaction of the contacted cells.

Further still, the invention comprises a method for detecting allergic reactions to a P14 allergen by administering a recombinant P14 of the invention to a subject, so as to provoke a bronchial, conjunctival, dermal, nasal or oral immunological reaction.

4. BRIEF DESCRIPTION OF THE FIGURES

The following figures and description aid in understanding the field and scope of the invention.

FIG. 1A: IgE immunoblot: Pollen proteins from birch (B), hornbeam (CA), alder (A) and hazel (C) were separated by means of a 12.5% polyacrylamide electrophoresis and blotted on nitrocellulose. The nitrocellulose was cut into strips (1–5) which were incubated with dilutions of a serum (1:5, 1:10, 1:20, 1:40, 1:80, respectively) of a selected patient whose IgE antibodies recognized most important birch pollen allergens. Arrows and stars indicate molecular weights. Bound serum IgE was detected by means of an autoradiograph of $^{125}$I-labeled antihuman IgE antibodies of rabbit bound thereto. The IgE-binding proteins of birch, alder, hazel and hornbeam matched one another, which demonstrates the similarity of the antigens.

FIG. 1B: IgE immunoblot inhibition: mugwort profilin that had been purified by poly(L-proline) affinity chromatography had been blotted on nitrocellulose after polyacrylamide gel electrophoresis. The 1:10 dilution of the serum from a patient allergic to birch profilin was pre-incubated in lane i with control proteins from *E. coli*, in lane 2 with recombinant birch profilin, in lane 3 with purified profilin from *Phleum pratense* (grass) and in lane 4 with buffer (negative control) and used for detection of mugwort profilin. Binding of patients' IgE to mugwort profilin can be blocked with recombinant birch profilin and purified grass profilin demonstrating common IgE binding properties of these related proteins. In the control lanes 1 and 4 binding of patients' IgE to mugwort profilin occurs.

Figure 2:
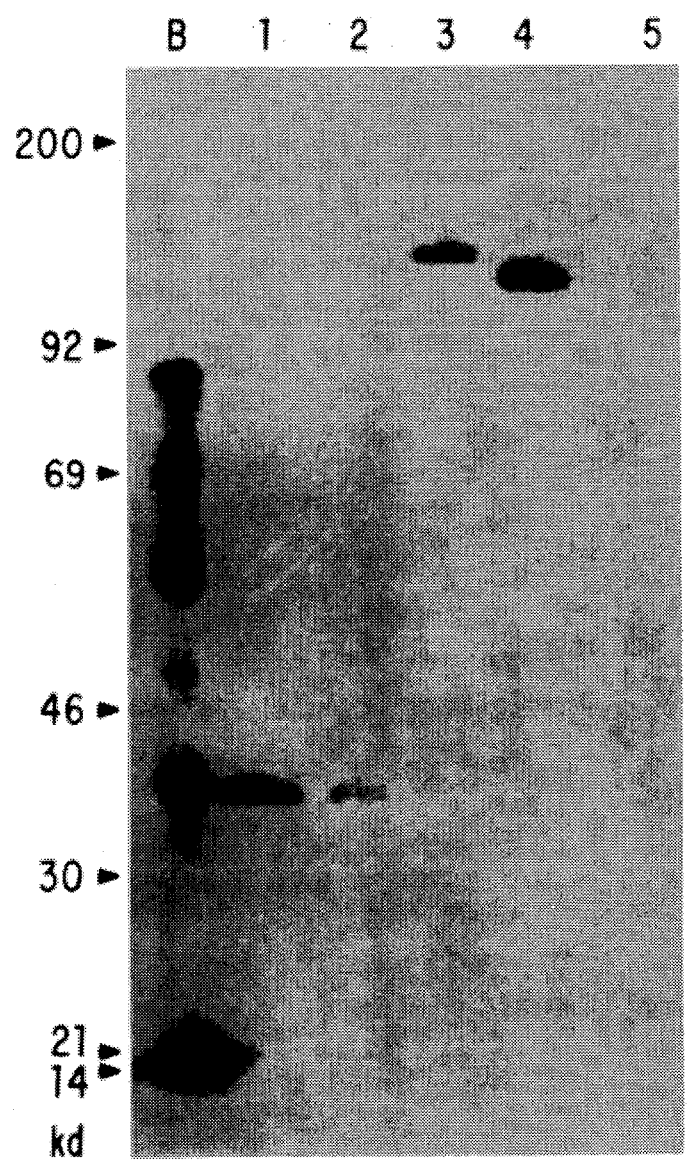

FIG. 2: IgE immunoblot: Proteins were separated by means of a 7.5% polyacrylamide gel electrophoresis and blotted on nitrocellulose. Lane B: birch pollen proteins; lane 1: proteins from *E. coli* Y1089 (lysogenic host); lane 2: proteins of *E. coli* Y 1089 inoculated with the lambda gt11 phage without insert; lane 3: proteins from *E. coli* Y1089 inoculated with a recombinant phage containing a birch pollen derived cDNA encoding an IgE binding polypeptide (positive control); lane 4: proteins from *E. coli* Y1089 inoculated with recombinant phages which contain the 3'-portion of P14 cDNA which codes for an IgE-binding epitope (as underlined in FIG. 4); lane 5: proteins from yeast (*Saccharomyces cerevisiae*). Recombinant β-galactosidase fusion proteins with IgE-binding capacity whose molecular weights were between 115 and 130 kD (lanes 3 and 4) were detected with $^{125}$-labeled antihuman IgE antiserum from rabbit. No comparable IgE binding takes place in lanes 1, 2 and 5, while lane B shows the patient's IgE-binding profile with birch pollen proteins.

Figure 3:
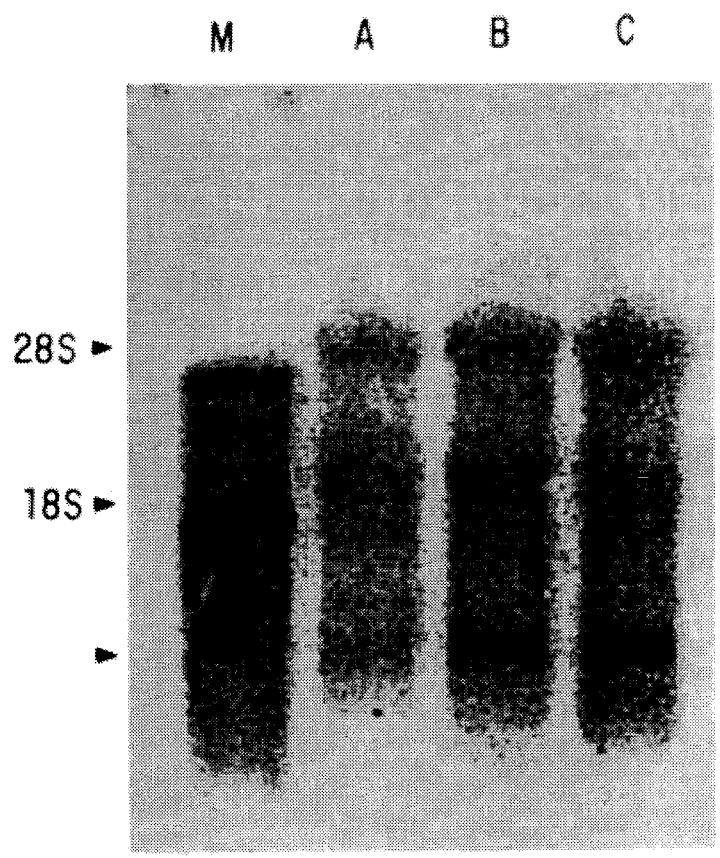

FIG. 3: Northern (RNA) blot: Ten μg pollen RNA of alder (lane A), birch (lane B) and hazel (lane C) and as a marker RNA of *E. coli* (lane M) were blotted on nitrocellulose. The part of the P14 cDNA underlined in FIG. 4 hybridizes with pollen mRNA of alder, birch and hazel and under stringent conditions (0.75×SSC, 0.1% SDS, 50° C.) produces a signal at 800 bases (indicated by an arrow). The position of ribosomal bands is indicated by "28S" and "18S".

FIG. 4: (SEQ ID NO:1) cDNA sequence of birch P14. The coding region begins with ATG (nucleotides 80–82) and ends with the stop codon TAG (nucleotides 479–481). The deduced amino acid sequence is illustrated under the DNA sequence. The P14 sequence, which within a fusion protein is able to bind IgE of patients and therefore represents at least one epitope, is shown underscored (see Section 5.4).

FIG. 5: Comparison of the derived amino acid sequence of birch P14 with the amino acid sequences of profilins of human (13), calf (14), mouse (12), yeast (11) and Acanthamoeba (10). Identical amino acid residues are marked. The percentage of identical amino acid residues between P14 protein of birch and homologs amounts to 30% for human protein, 28% for homologous proteins of calf and mouse, 26% for yeast protein and 25% for Acantbamoeba protein.

Figure 6:
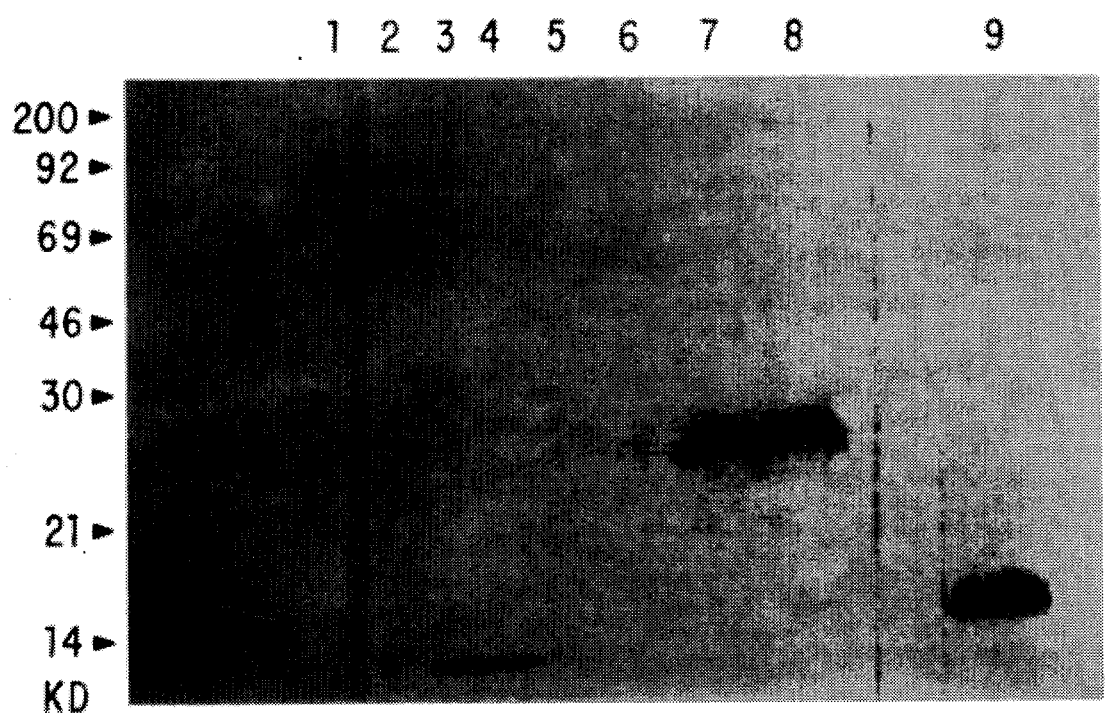

FIG. 6: Western (protein) blot of a polyacrylamide gel probed with IgE antibodies of patients with tree pollen allergy. Lane 1: proteins of *E. coli* JM105 without any plasmid; lane 2: proteins of *E. coli* JM105 with the plasmid pKK223-3 without an insert; lanes 3 and 4: proteins of *E. coli* JM105 with that plasmid derived from pKK2 23-3 which expresses the P14 protein of the inserted cDNA as nonfusion protein; lane 5: *E. coli* AR58 proteins; lane 6: *E. coli* AR58 with the plasmid pEXB without an insert; lanes 7 and 8: extracts from *E. coli* AR58 transformed with the plasmid derived from pEXB which expresses P14 cDNA as fusion protein; lane 9: birch pollen protein extract (positive control).

Figure 7:
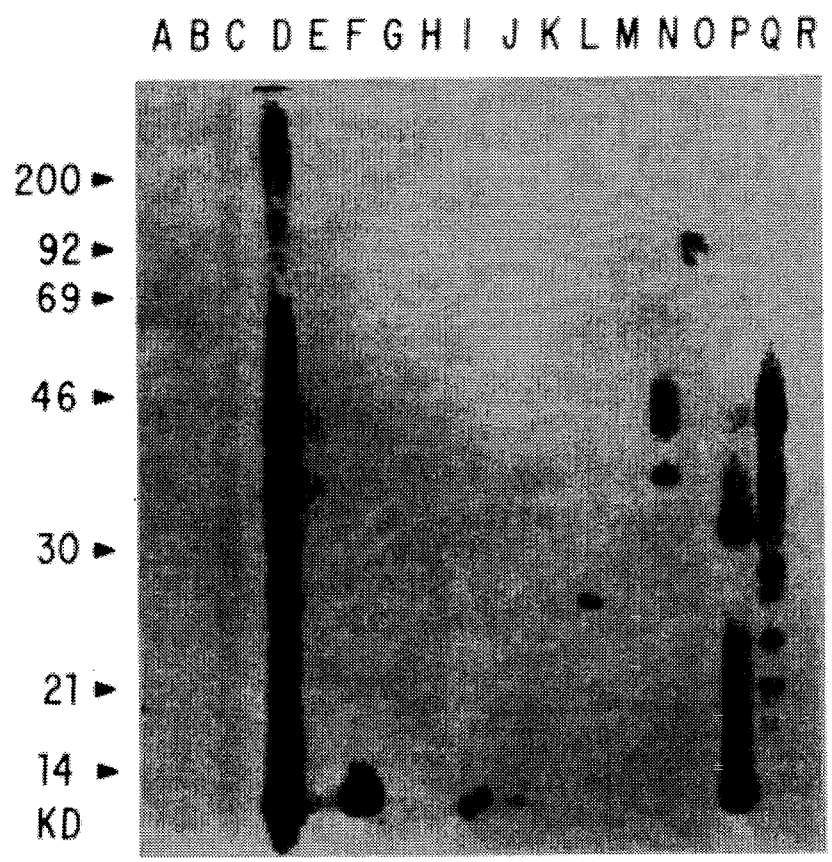

FIG. 7: Sera from various allergic patients were tested for their IgE reactivity with respect to recombinant P14 which was expressed in pKK223-3. Patients (lanes) D, E, F, I, J, and P show IgE binding to the recombinant P14. Lane R is a serum pool from non-allergic individuals. The recombinant P14 was not purified and, therefore, reactivity of patients' IgE with proteins from *E. coli* was seen.

Figure 8:
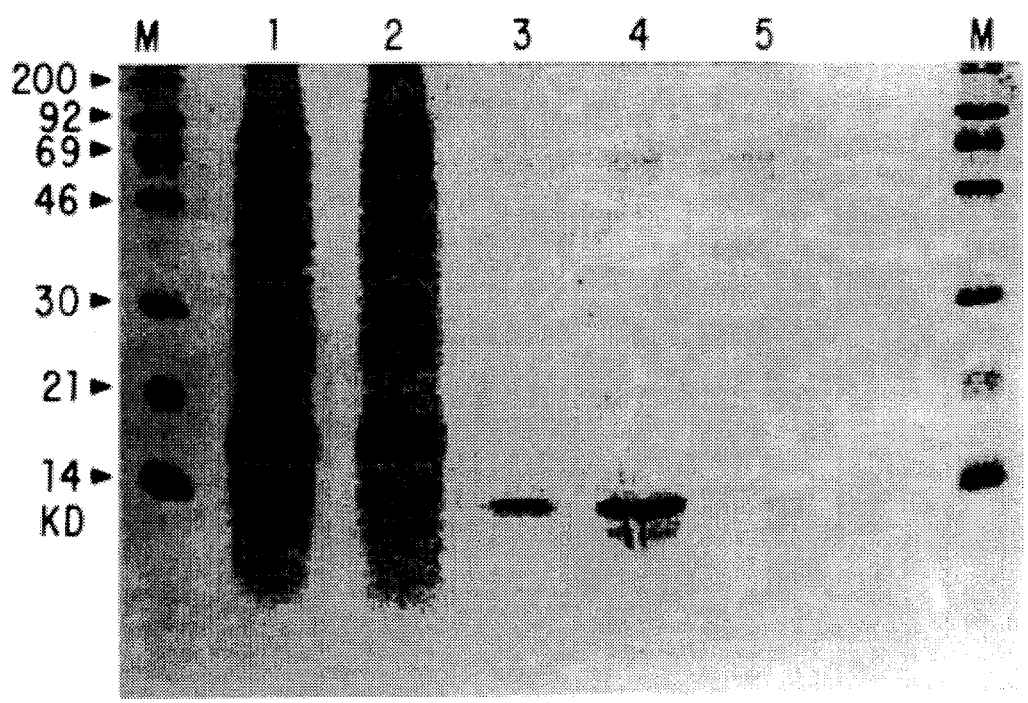

FIG. 8: Coomassie stained polyacrylamide gel. Lane M: molecular weight marker; lane 1: total pollen proteins of birch; lane 2: birch pollen proteins from which P14 was removed by the affinity method (flow through); lanes 3, 4 and 5: eluted P14. Proteins were applied to the gel and stained to indicate migration. As can be seen from lanes 3, 4 and 5, P14 can be purified by affinity chromatography to poly(L-proline) sepharose.

Figure 9:
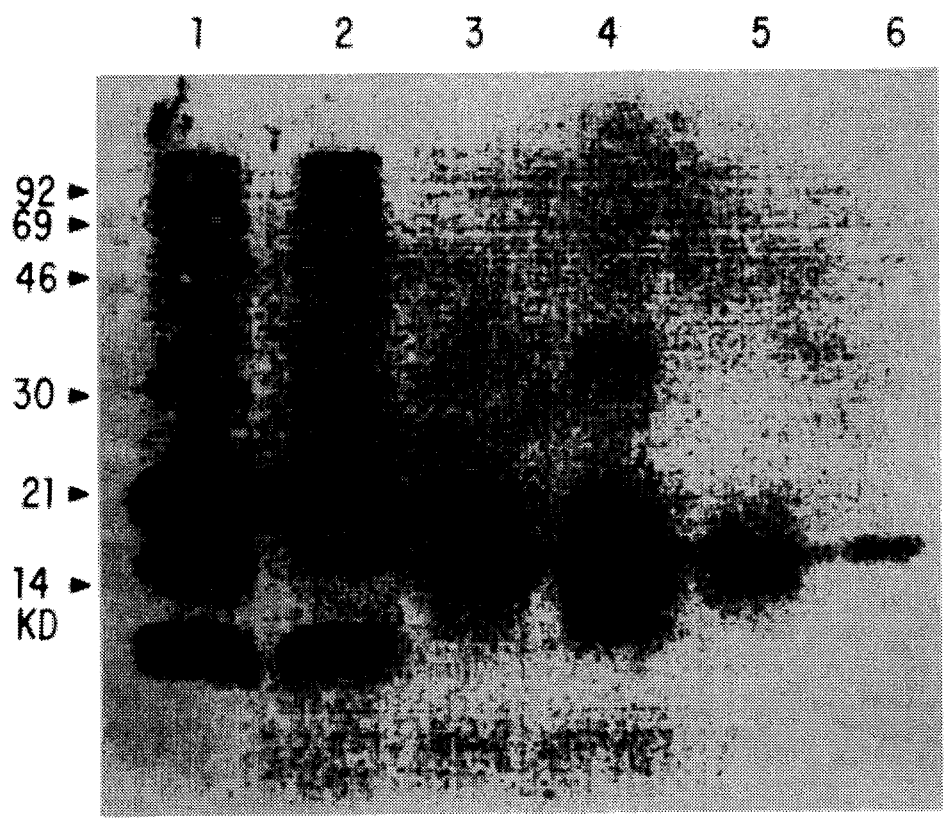

FIG. 9: IgE immunoblot: A probe of proteins obtained in the same way as in FIG. 8 was transferred to nitrocellulose and incubated with serum IgE of a patient who recognizes most birch pollen allergens. Lanes 1–5 contain the same material as in FIG. 8; lane 6 contains the molecular weight marker. This immunoblot shows that birch profilin can be purified to apparent homogeneity from other allergens.

Figure 10:
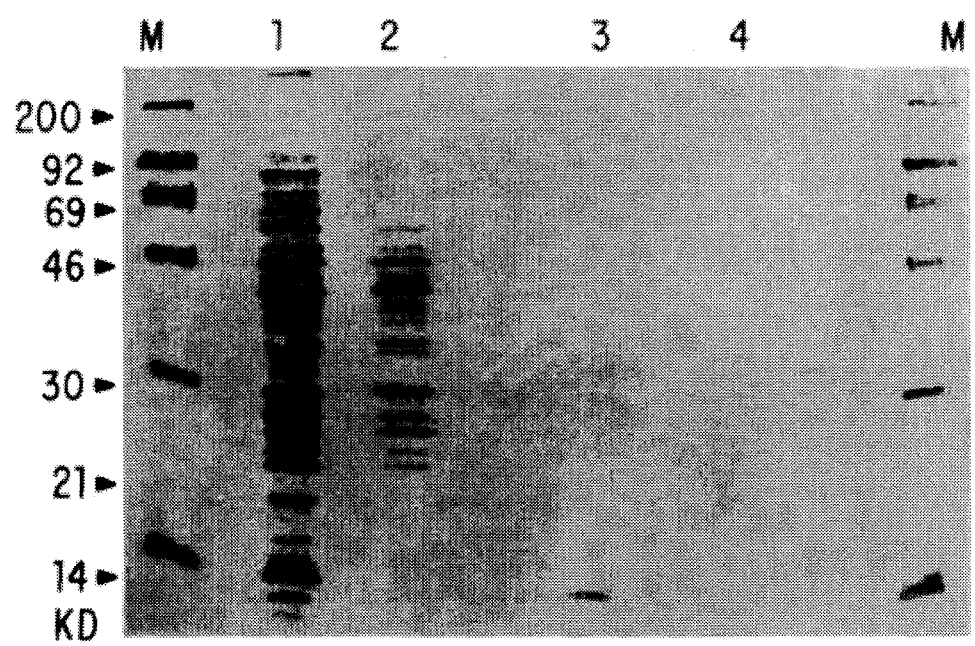

FIG. 10: Coomassie-stained polyacrylamide gel. Lane M: molecular weight marker; lane 1: total proteins of *E. coli* JM105 with the plasmid derived from pKK223-3 that expressed the P14 cDNA; lane 2: protein fraction after removal of the recombinant P14 by affinity chromatography to poly(L-proline) sepharose; lanes 3 and 4: purified recombinant P14-eluted fractions.

Figure 11:
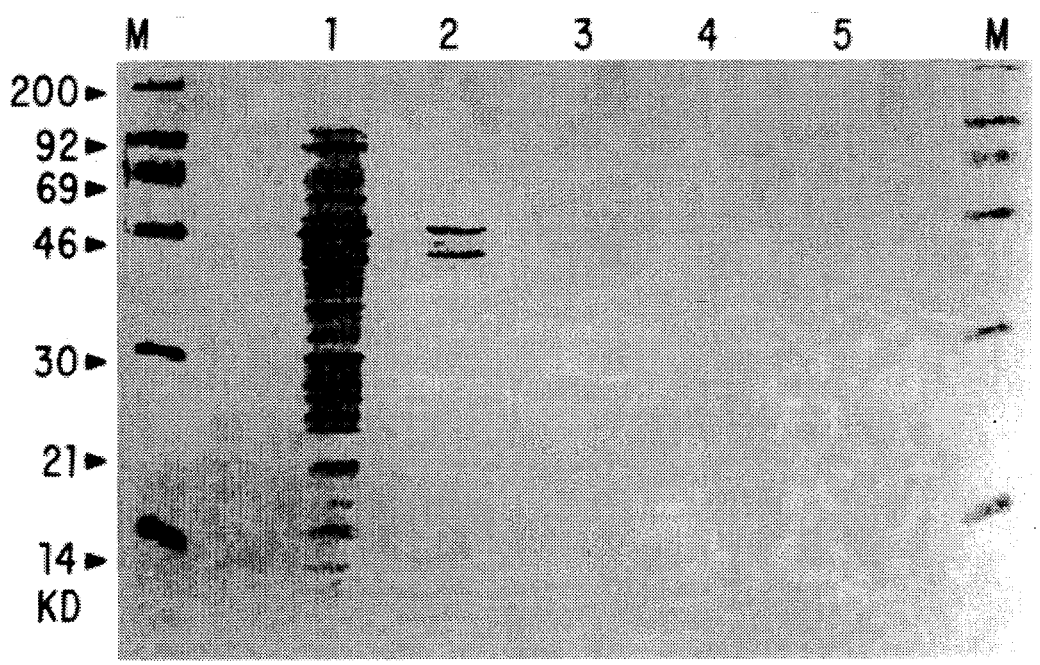

FIG. 11: Coomassie-stained polyacrylamide gel. Lane M: molecular weight marker; lane 1: total protein from *E. coli* JM105 with the plasmid pKK223-3 without insert; lane 2: protein fraction after poly(L-proline) purification; lanes 3, 4 and 5: eluted fractions. These results show that no protein with similar properties to P14 can be isolated from the expression system without insert.

FIG. 12: IgE immunoblot: Purified human profilin was loaded on a 12% polyacrylamide gel and blotted on nitrocellulose. Strips of the nitrocellulose were cut and incubated as follows: Strip 1 was incubated with serum IgE of a patient who recognized besides P14 and the major birch pollen allergen, Bet v I, allergens in the molecular range between 30 and 90 kD. Strip 2 was incubated with serum IgE from a patient who recognized only P14 in birch pollen extracts; strip 3 was incubated with serum from a patient whose serum IgE was directed only against Bet v I; strip 4 was incubated with the serum from a patient allergic to mites; strip 5 with serum from a group of nonallergic donors and strip 6 shows the buffer control. IgE binding was detected with a $^{125}$I-labeled antihuman IgE antiserum of rabbit. Cross-reactivity was shown for strips 1 and 2. This data demonstrates that serum IgE that reacts with birch pollen also cross-reacts with human profilin.

Figure 13:
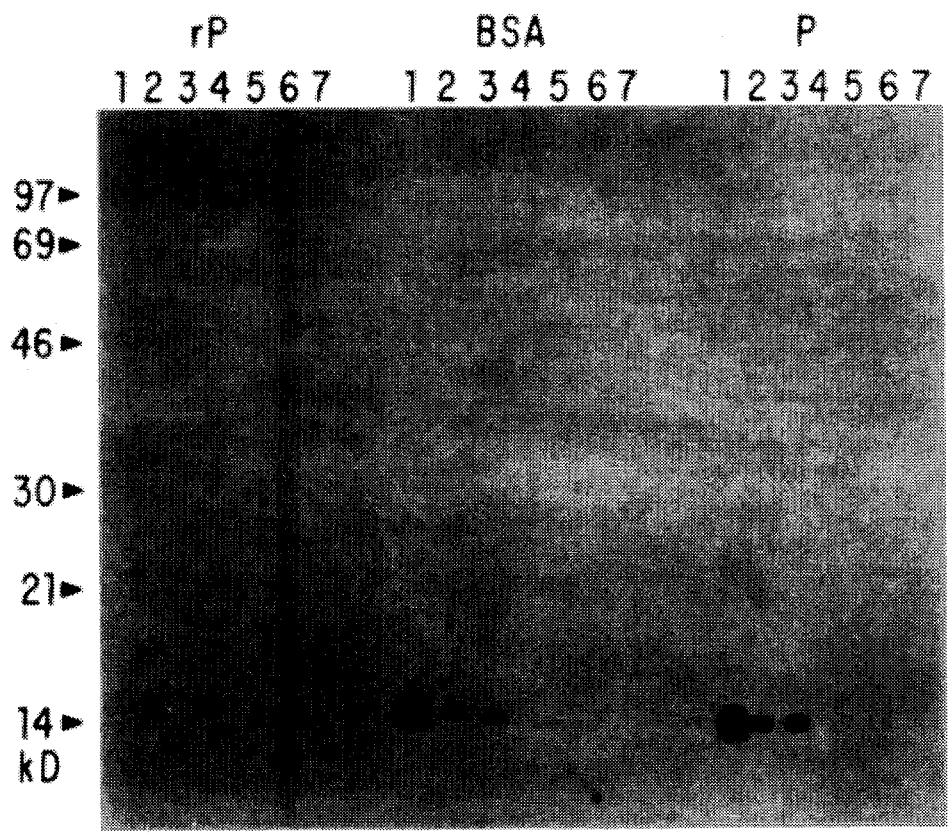

FIG. 13: IgE-inhibition: Purified celery profilin was subjected to SDS-Page, blotted to nitrocellulose (1μg/cm). Nitrocellulose strips where incubated with 1:10 dilutions of sera from birch pollen profilin allergic patients (lanes 1–3), from patients allergic to the major birch pollen allergen Bet v I but not to profilin, a serum pool of nonallergic individuals (lane 4) and with buffer without addition of serum (lane 5). The serum dilutions where preincubated with 5 μg of purified recombinant birch profilin each (rP), 5 μg of BSA (BSA), and with serum dilution buffer(P). Binding of IgE of the patients 1–3 to celery profilin can be blocked with purified recombinant birch profilin indicating common IgE epitopes of birch and celery profilin.

Figures 14A, 14B:
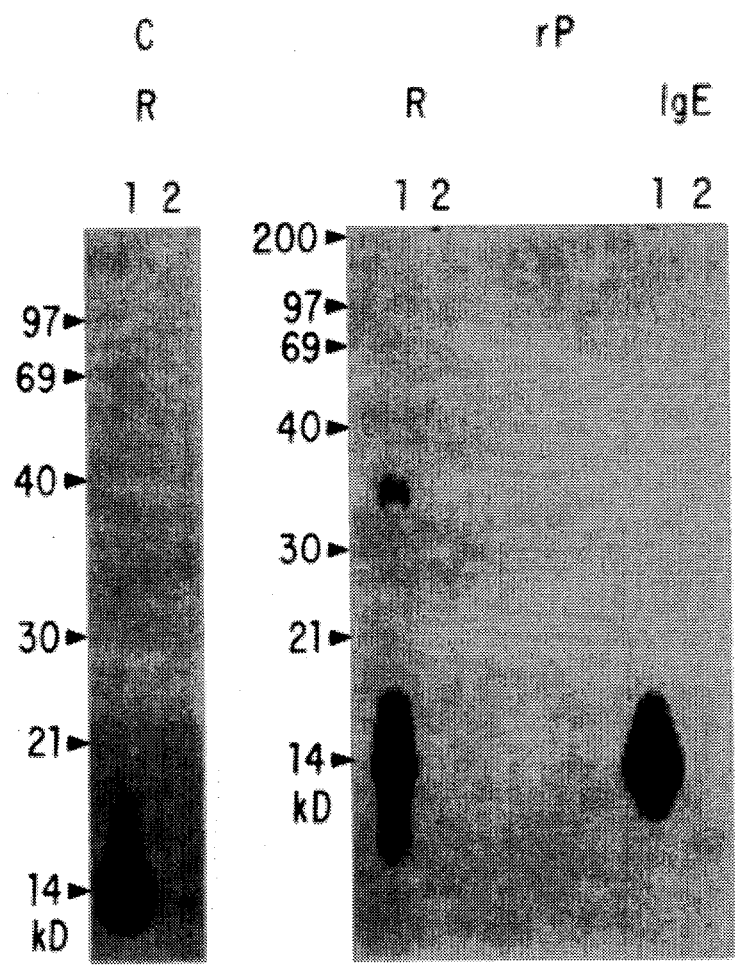

FIG. 14: Immunoblots: Purified celery profilin (C) and recombinant birch profilin (rP)is recognized by the rabbit anti celery profilin antibody (R: lane 1). Recombinant birch profilin also binds patients IgE (IgE: lane 1). No binding is seen in lane 2 (buffer control without addition of antibody or serum).

Figures 15A, 15B:
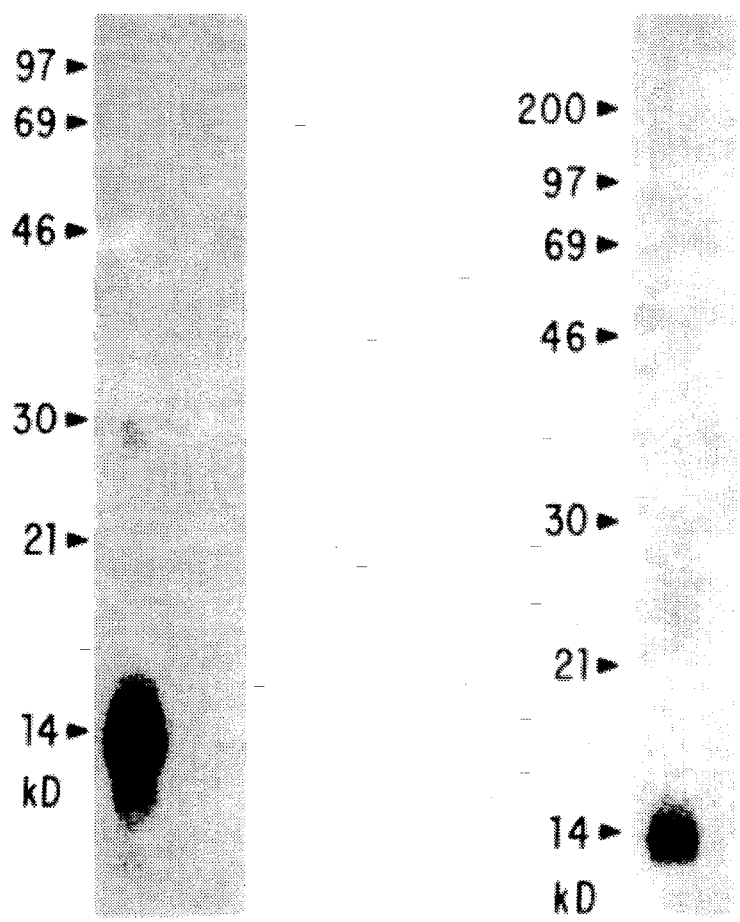

FIG. 15: Immunoblots: Purified profilin from rye (*Secale cereale* S) and from mugwort (*Artemisia vulgaris* M) binds the rabbit anti celery profilin antibody (lanes 1) whereas in the buffer control (lane 2) no binding was found.

Bound rabbit antibody in FIGS. 14 and 15 was detected with [125] J donkey anti rabbit antibody from Amerham, UK. Bound serum IgE in FIGS. 13 and 14 was detected with [125] J rabbit anti human IgE from Pharmacia, Sweden.

FIG. 16: cDNA and deduced amino acid sequence of profilin from pollen of timothy grass (*Phleum pratense*)

Figure 17:
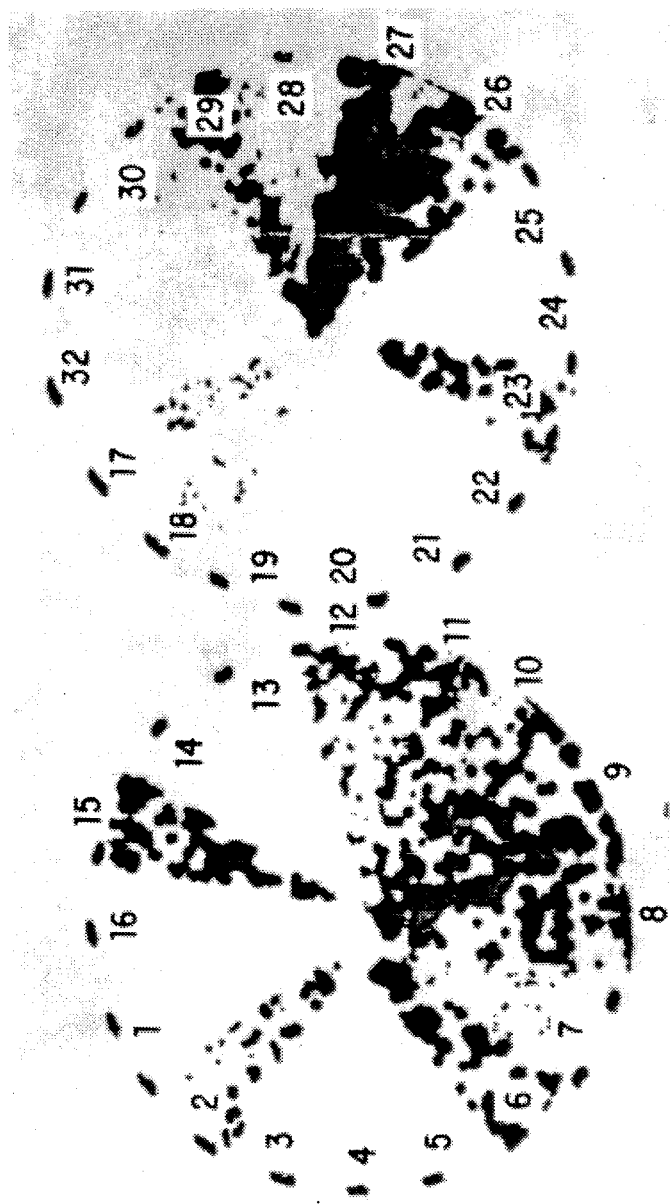

FIG. 17: IgE-binding of patients IgE to plaquelifts of lambda gt11 phages containing the cDNA insert encoding timothy grass profilin 30 grass pollen allergic patients were tested for IgE binding to lambda gt11 phages that express profilin from timothy grass which was bound to nitrocellulose sectors. Sector 31 shows a serumpool from non allergic individuals and sector 32 the buffer control without addition of serum. Serum IgE of patients 2, 6, 7, 8, 9,10,11,12,15, 17,18,21,23,26,27,28,29 and 30 bound to the recombinant timothygrass profilin expressed in lambda gt11. All these patients also displayed IgE reactivity to birch profilin. Patients 1, 3, 4,5,13,14,16,19,20,22,24, and 25 who were allergic to other grass pollen allergens did not show any IgE reactivity to timothy grass profilin. Bound serum IgE was detected as described in FIG. 13.

5. EXAMPLES

The invention can be understood by reference to the following examples:

5.1. Construction of the cDNA gene bank

Pollen (Allergon AB Engelholm, Sweden) which was examined for purity by means of light and electron microscopy, was used for the isolation of polyadenylated RNA (17, 18). cDNA synthesis was carried out with oligo-dT and random primers (19, 20), the ends of the cDNA were cleanly digested with T4-polymerase and provided with EcoRI-linkers. The cDNA with linkers was ligated and packed in dephosphorylated lambda gt11 arms (21). A cDNA gene bank of 800,000 independent clones was produced.

5.2. Screening of the cDNA gene bank

IgE screening of the birch pollen cDNA gene bank was performed as described (22). IgE-binding clones were enriched and phage DNA was prepared therefrom (23). The inserts were cut Out with EcoRI and the fragments were subcloned in the plasmid pUC18 (24). The DNA sequence of a clone was obtained (25). Although it was complete at the 3'-terminus (poly-A tail), it lacked a part of the 5'-terminus including the start codon as well. This partial sequence is underscored in FIG. 4. Therefore the original gene bank was again screened with oligodeoxynucleotides which were complementary to the coding region (26) and two independent clones were obtained.

5.3. RNA (Northern) blots

Ten µg of total RNA from pollen of alder, birch and hazel were separated by means of a denaturing gel electrophoresis and blotted on nitrocellulose (27, 28). A P14 cDNA probe, as underlined in FIG. 4, (SEQ ID NO: 1) was $^{32}$p-labeled by means of random priming (29). Prehybridization and hybridization were carried out by standard methods (23). The blots were washed with 0.75×SSC (20×SSC =3M NaCl, 0.3M Na citrate, pH 7.0 ), 0.1% SDS (sodium dodecyl sulfate) at 50° C. and autoradiographed (Hyperfilm MP, Amersham, London, UK).

Expression of Birch P14 cDNA

5.4.1 Expression of the 3'-terminus of the cDNA in lambda gt11 phages (FIG. 2)

An incomplete cDNA clone which codes for a part of P14 was obtained by means of IgE screening (22) as described in Section 5.2. The lysogenic *E. coli* strain Y1089 was inoculated with recombinant lambda gt11 phages, containing an insert as underlined in FIG. 4, and the β-galactosidase fusion protein was recovered from the mixture (19). The construction would predict that a fusion protein having a molecular weight of 116 kD would be produced. The mixture was subjected to electrophoresis on a 7.5% polyacrylamide gel and was blotted on nitrocellulose. The fusion protein was detected by means of IgE antibodies in patient serum and an iodine-labeled rabbit antihuman IgE antibody (Pharmacia, Uppsala, Sweden) (FIG. 2). As shown in FIG. 2, a fusion protein having a molecular weight of between 115 kD and capable of binding to IgE antibodies was observed.

5.4.2. Expression of complete P14 cDNA as fusion and nonfusion protein

The complete cDNA that codes for P14 contains a prokaryotic ribosome binding site (Shine-Dalgarno sequence (30)) and was inserted into the EcoRI sites of plasmids pKK223-3 (31) or pEXB (32) to obtain P14 as a nonfusion protein or a fusion protein of P14 with the lambda cII protein. IgE-binding clones were obtained by means of serum IgE and a colony screening method (33) and were examined by means of DNA restriction analysis. Recombinant proteins were tested for their binding capacity with respect to patient IgE antibodies as described (22) (FIG. 6).

5.5. Purification of birch pollen P14 and recombinant P14

P14 from birch pollen and recombinant P14 were purified by means of an affinity method by a batch process (cf. 15, 16) which is suitable for the profilins of Acanthamoeba (10), yeast (11) and man (13). Birch pollen and *E. coli* cells, which contain the plasmid that codes for P14, were lysed in PHEM-TX buffer (2×PHEM-TX: 120 mM PIPES (piperazine-1,4-bis(2-ethanesulfonic acid)), 50 mM HEPES (N-2-hydroxyethylpiperazine-N'-2-ethanesulfonic acid), 20 mM EGTA (ethylene glycol-bis(β-aminoethyl ether)-N,N,N',N'-tetraacetic acid), 4 mM $MgCl_2$, 10 mM glucose, 20 µg/ml leupeptin, 156 µg/ml benzamidin, S80 µg/ml aprotinin, 1 mM PMSF (phenylmethyl sulfonyl fluoride), 1.5% Triton-X100, pH 7.2) and the lysate was centrifuged for one hour at 65000×g at 4° C. The supernatant was incubated overnight at 4° C. with poly(L-proline) coupled to BrCN-activated Sepharose 4B (Pharmacia, Uppsala, Sweden). Then the affinity matrix was washed three times with a double volume each time of TBS-ATP (20 mM TRIS, 150 mM NaCl, 0.5 mM ATP (adenosine triphosphate), pH 7.6) and then eluted for five minutes at room temperature with a double volume of elution buffer I (TBS-ATP with 2M urea). The supernatant was collected. The procedure was repeated twice with elution buffer II (TBS-ATP with 6M urea) and the supernatants were dialyzed against distilled water at 4° C. The dialysates, which contained the proteins, were lyophilized and analyzed by means of polyacrylamide gel electrophoresis and IgE immunoblot (FIGS. 8, 9, 10 and 11).

5.6. IgE-binding capacity of a protein expressed from a fragment of P14 cDNA which contains an IgE-binding epitope The 3'-region of P14 cDNA (bp 419–478) was cloned in the EcoRI site of lambda gt11 and expressed as an IgE-binding polypeptide (21) as shown in FIG. 2. The β-galactosidase fusion protein (lane 4) bound strongly to IgE of the patient, while the control lanes 1 and 2 exhibited no IgE binding for the proteins of *E. coli* Y1089 and the proteins of *E. coli* Y1089 which were inoculated with lambda gt11 phages without an insert. This example shows that a partial cDNA clone which codes for a protein having at least one epitope of the P14 molecule was obtained. It follows from this that partial cDNA clones which code for such incomplete P14 polypeptides may be useful for a therapy or diagnosis in a way similar to the complete P14 molecule or homologous proteins.

5.7. Demonstration of polynucleotides and polypeptides homologous to P14 within the order Fagales The Northern (RNA) blot (FIG. 3) shows that the P14 cDNA sequence (polynucleotide underlined in FIG. 4) is able to cross-hybridize with pollen mRNA from alder and hazel under stringent conditions (requirements of stringency are defined in 3. Summary of the Invention). Therefore, the sequence homology of the corresponding allergens of trees of the order Fagales can already be demonstrated at the nucleic acid level. FIG. 1A already showed a similar IgE-binding capacity of proteins of alder, hazel and hornbeam homologous to P14. It follows from this that P14 cDNA codes for polypeptides of similar IgE-binding capacity and antigenicity to closely related tree pollen allergens.

5.8. Sequence analysis

FIG. 4 shows the sequence of the cDNA that codes for birch P14, and the deduced amino acid sequence of the coding-region. It contains the complete protein coding region. The sequence of the peptide that, coupled to β-galactosidase, represents an IgE-binding epitope is underlined in the figure (see Example 5.4).

FIG. 5 illustrates the sequence homology between the P14 protein of birch and of human, mouse, calf, yeast and Acanthamoeba profilins (13, 12, 14, 11, 10).

The cross-reactivity of patient IgE with birch P14 and human profilin is shown in FIG. 12. Similar chemical properties of these related proteins were likewise shown by their common affinity to poly(L-proline) (FIGS. 8 and 10). These data indicate that the profilins of species which are as far apart in evolutionary terms as humans and birch are able to act as cross-reactive panallergens that may lead to an IgE autoimmune reactivity in patients.

5.9. Expression of P14 coding cDNA in E. coli as fusion or nonfusion protein and detection of IgE-binding capacity of these polypeptides The polynucleotide given in FIG. 4 (SEQ ID NO: 1)(nucleotides 1–710) that codes for birch P14 was inserted in the plasmid pKK223-3 so that a recombinant nonfusion protein (31) could be prepared, while a recombinant fusion protein was produced in the plasmid pEXB (32). The reactivity of these polypeptides with patient IgE is shown in FIG. 6. Control protein extracts of E. coli in lanes 1, 2, 5 and 6 do not bind IgE, while recombinant birch P14 expressed as a nonfusion protein (lanes 3 and 4) and as a fusion protein (lanes 7 and 8) does bind IgE.

In FIG. 7, sera from persons allergic to birch pollen (A–K), to grass pollen (L–N) and to mugwort —Q) and of a pool of nonallergic individuals (R), all of whom had been selected according to their case history, RAST and skin test, were tested for their IgE-binding capacity with recombinant birch P14. IgEs of Sera D, E, F, I, J and P bound to P14 expressed in pKK223-3.

It follows from this that this invention provides a polynucleotide that codes for polypeptides which have similar antigenicity and similar IgE-binding capacity to the P14 protein of birch when the polynucleotide is inserted in the correct reading frame of a variety of expression systems. The IgE-binding properties of these polypeptides were demonstrated for sera from patients who exhibit allergic reactions to various pollens and hence point to the great clinical significance of these polypeptides (FIG. 7).

5.10. Purification of P14 from pollen and of recombinant P14 from E. coli

As described above, this invention provides a simple method for purifying natural as well as recombinant P14. The Coomassie-stained polyacrylamide gel in FIG. 8 shows that pure P14 (lanes 3, 4 and 5) can be separated from total pollen protein (lane 1). The proteins which do not bind to poly(L-proline)-Sepharose are also shown (lane 2). The effectiveness of this purification method was monitored by means of IgE immunoblotting (FIG. 9), and for this purpose serum from a patient who recognizes most birch pollen allergens with IgE antibodies (lane 1) was used. After application of the affinity method, almost no P14 can be found (lane 2), while purified P14 was obtained in lanes 3, 4 and 5.

FIG. 10 shows a polyacrylamide gel which demonstrates the purification of recombinant P14 from E. coli JM105 that is transformed with the plasmid pKK223-3, which carries the P14 coding sequence. Recombinant P14 (lanes 3 and 4) was purified from the total proteins by affinity chromatography to poly(L-proline) sepharose (lane the remaining proteins being shown by lane 2. FIG. 11 shows that no homologous protein from E. coli JM105 transformed with pKK223-3 without insert is obtained by means of the method used.

As FIGS. 9, 6 and 7 show, the purified protein (from birch and E. coli) retains its IgE-binding capacity. This example thus shows that the present invention likewise provides a simple and rapid purification method for P14 both as natural and recombinant polypeptide. Using poly(L-proline) to purify, both natural and recombinant P14 retain their antigenicity and IgE binding capacity. In addition, the method offers the opportunity to immobilize (and separate by affinity means) the immunologically active polypeptide.

5.11. IgE reactivity of allergic and atopic patients with human profilin

Various patient sera were selected as follows (FIG. 12): Patient 1 shows IgE antibodies which are directed against most birch pollen allergens, including BetvI and P14, patient 2 shows IgE binding only with P14 and patient 3 only with BetvI. Patient 4 is a person allergic to house dust mite and the serum pool 5 was made up of nonallergic individuals. Strip 6 is the buffer control. All these sera were tested for their IgE-binding capacity with nonrecombinant and recombinant P14 and human profilin. Those patients (FIG. 12), who recognized the nonrecombinant P14 from birch as well as the recombinant P14 from E. coli, also had IgE antibodies against human profilin. For this reason, this invention for the first time gives indications on the molecular level that autoimmune mechanisms might play a role in atopic and allergic diseases. Since patients with other autoimmune diseases form antibodies against P14, this invention should provide a diagnostic marker for these diseases.

5.12. Correlation of case histories of atopic and allergic patients with the binding of IgE antibodies to P14

The case histories of patients who form IgE antibodies against P14 show that all of them suffer from severe allergic symptoms which are caused by a great variety of allergens (tree and grass pollen, mite, cat and dog allergens), that they have an elevated total IgE level and show an unsatisfactory course in hyposensitization therapy. It follows from this that a positive reaction of the serum IgE of patients with P14 is usable as a good marker for the differentiation of certain groups of atopic and allergic patients.

5.13. Demonstration of common IgE-epitopes between profilins in food (celery) and pollen P14 allergen (birch).

The IgE-inhibition experiment shown in FIG. 13 shows that there is common IgE-binding capacity of proteins homologous to the P14 allergen in pollens and food. Purified recombinant birch profilin, when added to the patients' serum in the fluid phase before the serum is incubated with the nitrocellulose bound celery profilin, is able to completely block the binding of patients' IgE to celery profilin. This indicates that the P14 allergen of birch (birch profilin) contains all IgE epitopes that can be found in celery profilin. Recombinant birch P14 allergen is therefore suitable not only for diagnosis and therapy of pollen allergies but also for food allergies.

Common antigenicity of birch pollen P14 allergen and food profilins is also shown by crossreactivity of a rabbit anti celery profilin antibody with the pollen P14 allergen (FIGS. 14 and 15).

5.14. Sequence similarity and common IgE-binding, capacity of pollen P14 allergen from white birch (*Betula verrucosa*) and the homologous P14(T) allergen from timothy grass (*Phleum pratense*).

Amino acid sequence identity of birch P14 allergen and timothy grass P14(T) allergen is 77%. The cDNA encoding the P14(T) allergen from timothy grass was obtained by screening a cDNA library, which was constructed from pollen of timothy grass in the same way as described for the cDNA library from birch pollen, with patients' IgE as described for the P14 allergen of birch. The cDNA sequence of the clone encoding the P14(T) allergen of timothy grass is shown in FIG. 16 and as sequences 9–11 in the sequence listing. All patients' sera that bound with their IgE to birch profilin also bound with their IgE to sectors of nitrocellulose filters containing plaquelifts of immunopositive lambda gt11 phages into which the cDNA encoding timothy grass P14(T) allergen had been inserted (FIG. 17). This shows that the proteins related to the P14 allergens by high homology also are immunologically cross reactive with patients' IgE antibodies.

6. METHODS OF ADMINISTRATION

The present invention covers the use of P14 synthetic polypeptide allergens to hyposensitize or desensitize a mammal. Such polypeptides can be administered to a human subject either alone or in combination with pharmaceutically acceptable carriers or diluents, in accordance with standard pharmaceutical practice.

The method of hyposensitization involves or could involve the successive parenteral, oral, nasal, inhalant or rectal administration of incremental doses of the P14 allergen. The term parenteral as used herein includes subcutaneous, intravenous or intramuscular injections.

A range from 1 picogram to 10 milligrams per application can be used. The diluents and carriers can be chosen by those skilled in the art according to commonly accepted galenic procedures.

7. REFERENCES

The references cited in the above specification are:

1. L. Yman, Botanical relations and immunological cross-reactions in pollen allergy, 2nd ed. Uppsala, Sweden: Pharmacia AB, 1982.

2. W. R. Thomas, K. Y. Chua, W. K. Greene and G. A. Stewart. Recombinant mite allergens. In: Epitopes of atopic allergens. A. H. Sehon, D. Kraft, and G. Kunkel (eds). UCB Institute of Allergy, Brussels 1990.

3. E. Jarolim, M. Tejkl, M. Rohac, G. Schlerka, M. Breitenbach, O. Scheiner, D. Kraft, H. Rumpold. Monoclonal antibodies against birch pollen allergens; characterization by immunoblotting and use for single step affinity purification of the major allergen BetvI. Int. Arch. Allergy Appl. Immunol. 90, 54–60(1989).

4. H. Ipsen, H. Bowadt, H. Janniche, B. Nüchel Petersen, E. P. Munch, J. A. Wihl and H. Lowenstein. Immunochemical characterization of reference alder (Alnus glutinosa) and hazel (Corylus avellana) pollen extracts and the partial immunochemical identity between the major allergens of alder, birch, and hazel pollen. Allergy 40, 510–518 (1985).

5. H. Rumpold, M. Rohac, B. Bohle, M. Breitenbach, O. Scheiner and D. Kraft. The relationship of BetvI epitopes recognized by patients' IgE and monoclonal anti-BetvI antibodies. In: Epitopes of atopic allergens. A. Sehon, D. Kraft and G. Kunkel (eds). The UCB Institute of Allergy, Brussels 1990.

6. R. Valenta, H. Breiteneder, K. Pettenburger, M. Breitenbach, H. Rumpold, D. Kraft and O. Scheiner. Homology of the major pollen allergens of alder, hazel, and hornbeam at the nucleic acid level as determined by cross-hybridization. J. Allergy Clin. Immunol., in press.

7. B. Nüchel Petersen, H. Janniche, E. P. Munch, J. A. Wihl, H. Bowadt, H. Ipsen and H. Lowenstein. Immunotherapy with partially purified and standardized tree pollen extracts. Allergy 43, 353–362 (1988).

8. J. A. Wihl, H. Ipsen, B. Nüchel Petersen, E. P. Munch, H. Janniche and H. Lowenstein. Immunotherapy with partially purified tree pollen extracts. Allergy 43, 363–369 (1988).

9. H. Ipsen, B. Schwartz, J. A. Wihl, B. Nüchel Petersen, E. P. Munch, H. Janniche and H. Lowenstein. Immunotherapy with partially purified and standardized tree pollen extracts. Allergy 43, 370–377 (1988).

10. C. Ampe, J. Vandekerckhove, S. L. Brenner, L. Tobacman and E. D. Korn. The amino acid sequence of Acanthamoeba profilin. J. Biol. Chem. 260, 834–840 (1985).

11. V. Magdolen, U. Oechsner, G. Mallet and W. Bandlow. The intron-containing gene for yeast profilin (PFY) encodes a vital function. Mol. Cell. Biol. 8, 5108–5115 (1988).

12. J. S. Widada, C. Ferraz and J.-P. Liautard. Total coding sequence of profilin cDNA from Mus musculus macrophage. Nucl. Acids Res. 17, 2855 (1989).

13. D. J. Kwiatkowski and G. A. P. Bruns. Human profilin. Molecular cloning, sequence comparison, and chromosomal analysis. J. Biol. Chem. 263, 5910–5915 (1988).

14. C. Ampe, F. Markey, U. Lindberg and J. Vandekerckhove. The primary structure of human platelet profilin: reinvestigation of the calf spleen profilin sequence. FEBS Lett. 228, 17–21 (1988).

15. Lindberg, C. E. Schutt, E. Hellsten, A. -C. Tjäder und T. Hult. The use of poly(L-proline)-Sepharose in the isolation of profilin and profilactin complexes. Biochim. Biophys. Acta 967, 391–400 (1988).

16. M. Tanaka and H. Shibata. Poly(L-proline)binding proteins from chick embryos are a profilin and a profilactin. Eur. J. Biochem. 151, 291–297 (1985).

17. H. Breiteneder, W. Hassfeld, K. Pettenburger, E. Jarolim, M. Breitenbach, H. Rumpold, D. Kraft and O. Scheiner. Isolation and characterization of messenger RNA from male inflorescences and pollen of white birch (*Betula verrucosa*). Int. Arch. Allergy Appl. Immunol. 87, 19–24 (1988).

18. H. Aviv und P. Leder. Purification of biologically active globin messenger RNA by chromatography on oligothymidylic acid-cellulose. Proc. Natl. Acad. Sci. USA 69, 1408–1412 (1972).

19. T. V. Huynh, R. A. Young, R. W. Davis, In: DNA cloning—a practical approach, Band 1, D. M. Glover (ed), IRL Press, Oxford 1985.

20. H. Haymerle. Nucl. Acids Res. 14, 8615 (1986).

21. R. A. Young and R. W. Davis. Efficient isolation of genes by using antibody probes. Proc. Natl. Acad. Sci. USA 80, 1184–1198 (1983).

22. H. Breiteneder, K. Pettenburger, A. Bito, R. Valenta, D. Kraft, H. Rumpold, O. Scheiner and M. Breitenbach. The gene coding for the major birch pollen allergen BetvI is highly homologous to a pea disease resistance response gene. EMBO J. 8, 1935–1938 (1989).

23. F. M. Ausubel. Current protocols in molecular biology. Green Publishing Associates and Wiley-Interscience, New York, 1987.

24. C. Yanisch-Perron, J. Vieira and J. Messing. Improved M13 phage cloning vectors and host strains: nucleotide sequences of the M13mp18 and pUC19 vectors. Gene 33, 103–119 (1985).

25. F. Sanger, S. Nicklen and A. R. Coulson. DNA sequencing with chain-terminating inhibitors. Proc. Natl. Acad. Sci. USA 74, 5463–5467 (1977).

26. R. B. Wallace, J. Shaffer, R. F. Murphy, J. Bonner, T. Hirose and K. Itakura. Hybridization of synthetic oligodeoxyribonucleotides to φX 174 DNA: the effect of a single base pair mismatch. Nucleic Acids Res. 6, 3543–3557 (1979).

27. P. S. Thomas. Hybridization of denatured RNA and small DNA fragments transferred to nitrocellulose. Proc. Natl. Acad. Sci. USA 77, 5201–5205 (1980).

28. H. Lehrach. RNA molecular weight determinations by gel electrophoresis under denaturing conditions: a critical reexamination. Biochemistry 16, 4743–4751 (1977).

29. A. P. Feinberg and B. Vogelstein. A technique for radiolabeling DNA restriction fragments to high specific activity. Anal. Biochem. 132, 6–13 (1983).

30. J. Shine and L. Dalgarno. The 3'-terminal sequence of *Escherichia coli* 16S ribosomal RNA: complementarity to nonsense triplets and ribosome binding sites. Proc. Natl. Acad. Sci. USA 71, 1342–1346 (1974).

31. E. Amann, J. Brosius and M. Ptashne. Vectors bearing a hybrid trp-lac promoter useful for regulated expression of cloned genes in *Escherichia coli*. Gene 25, 167–178 (1983).

32. N. Kiyoshi, H. C. Thøgersen. Generation of β-globin by sequence-specific proteolysis of a hybrid protein produced in *Escherichia coli*. Nature 309, 810–812 (1984).

33. D. M. Helfman, J. R. Feramisco, J. C. Fiddes, G. P. Thomas and S. H. Hughes. Identification of clones that encode chicken tropomyosin by direct immunological screening of a cDNA expression library. Proc. Natl. Acad. Sci. USA 80, 31–35 (1983).

What is claimed is:

1. A recombinant DNA molecule consisting of the sequence of SEQ ID NO:2.

2. A replicable microbial expression vehicle which directs expression of a DNA of claim 1 to produce said protein.

3. A prokaryotic host cell containing a DNA according to claim 1, wherein said DNA replicates and expresses the P14 allergen.

4. A recombinant DNA molecule encoding a protein consisting SEQ ID NO:3.

5. A recombinant DNA molecule consisting of sequence of SEQ ID NO:1.

6. A recombinant DNA molecule, comprising DNA that is complementary to a nucleic acid molecule that hybridizes under stringent conditions to a DNA molecule consisting of the nucleic acid sequence of SEQ ID NO:2 and which encodes a protein that (a) binds to IgE antibodies in serum of an individual allergic to an allergen consisting of the amino acid sequence of SEQ ID NO:3 and (b) binds to poly-(L-proline), wherein said stringent conditions are: at 55° C., a salt concentration of 150 mM NaCl and 15 mM Na$_3$citrate×2H$_2$O, at pH 7.0 and with sodium dodecyl sulfate at a concentration of 0.1% weight/volume.

7. A recombinant DNA molecule according to claim 6, wherein the protein is a P14 allergen selected from the group consisting of birch, alder, hazel, hornbeam and oak.

8. A recombinant DNA molecule according to claim 6, wherein the protein is a P14 allergen of birch.

9. A recombinant DNA molecule according to any one of claims 6, 7 or 8 which codes for a protein consisting of the amino acid sequence of SEQ ID NO:3.

10. A replicable microbial expression vehicle which directs expression of a DNA of any one of claims 6, 7, or 8 to produce said protein.

11. A replicable microbial expression vehicle which directs expression of a DNA of claim 9 to produce said protein.

12. A prokaryotic or eukaryotic host cell containing a microbial expression vehicle which directs expression of a DNA of any one of claims 6, 7 or 8 to produce said protein.

13. A prokaryotic or eukaryotic host cell containing a microbial expression vehicle which directs expression of a DNA of claim 9 to produce said protein.

14. A host organism according to claim 12, wherein the host cell is *Escherichia coli*.

15. A host organism according to claim 13, wherein the host cell is *Escherichia coli*.

* * * * *